United States Patent
Heyn et al.

(10) Patent No.: US 7,745,687 B2
(45) Date of Patent: Jun. 29, 2010

(54) ABSORBENT ARTICLE WITH REINFORCED ABSORBENT STRUCTURE

(75) Inventors: David W. Heyn, Neenah, WI (US); Matthew J. Barron, Rock, MI (US); Sonya L. Eggen, Minneapolis, MN (US); Amber M. Fortune, Kaukauna, WI (US); Robert E. Gee, Aiken, SC (US); Eric D. Johnson, Larsen, WI (US); James M. Kaun, Neenah, WI (US); Dean M. Laux, Appleton, WI (US); Toan T. LeMinh, Greenville, WI (US); Billie D. Matelski, Neenah, WI (US); Shannon K. Melius, Appleton, WI (US); Melanie J. Milslagle, Appleton, WI (US); Angie M. Provost, Appleton, WI (US); Kenneth R. Schueler, Jr., Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1351 days.

(21) Appl. No.: 10/306,086

(22) Filed: Nov. 27, 2002

(65) Prior Publication Data
US 2003/0171728 A1 Sep. 11, 2003

Related U.S. Application Data

(60) Provisional application No. 60/350,079, filed on Jan. 15, 2002.

(51) Int. Cl.
*A61F 13/15* (2006.01)
*A61F 13/20* (2006.01)

(52) U.S. Cl. ...................... 604/367; 604/378
(58) Field of Classification Search ......... 604/367–378, 604/381, 385.01
See application file for complete search history.

(56) References Cited

U.S. PATENT DOCUMENTS

| | | | |
|---|---|---|---|
| 2,161,539 A | 6/1939 | Swartz |
| 2,964,039 A | 12/1960 | Johnson, Jr. et al. |
| 3,085,309 A | 4/1963 | Olson |
| 3,156,751 A | 11/1964 | Valdes et al. |
| 3,587,579 A | 6/1971 | Sabee |
| 3,629,047 A | 12/1971 | Davison |
| 3,683,921 A | 8/1972 | Brooks et al. |
| 3,768,479 A | 10/1973 | Widlund |
| 3,816,231 A | 6/1974 | Marshall |
| 3,856,012 A | 12/1974 | MacDonald et al. |
| 3,862,877 A | 1/1975 | Camden |
| 3,867,935 A | 2/1975 | Eisdorfer et al. |
| 3,888,248 A | 6/1975 | Moore et al. |
| 3,935,979 A | 2/1976 | Hickey |
| 4,001,472 A | 1/1977 | Thomas et al. |

(Continued)

FOREIGN PATENT DOCUMENTS

AU 458424 2/1975

(Continued)

OTHER PUBLICATIONS

International Search Report, dated May 28, 2003 in PCT/US 03/00881, 8 pages.

(Continued)

*Primary Examiner*—Michele Kidwell
(74) *Attorney, Agent, or Firm*—Armstrong Teasdale, LLP

(57) ABSTRACT

An absorbent structure can include a matrix of fibers, wherein the matrix is reinforced with a reinforcing member, such as scrim. Preferably, the scrim is secured to the fibrous matrix by entanglement of fibers with the scrim and entanglement of fibers in the matrix from opposite sides of the scrim with each other. The scrim layer can be restricted to a longitudinally extending, medial region of the absorbent. In a particular arrangement, the scrim has a cross-directional width dimension which is less than a narrowest width dimension of the fibrous matrix. The scrim can be located between two, opposed, major surfaces of the fibrous matrix.

32 Claims, 15 Drawing Sheets

U.S. PATENT DOCUMENTS

| | | | |
|---|---|---|---|
| 4,028,455 A | 6/1977 | Ueda et al. | |
| 4,141,772 A | 2/1979 | Buell | |
| 4,217,078 A | 8/1980 | Buell | |
| 4,235,237 A | 11/1980 | Mesek et al. | |
| 4,300,562 A | 11/1981 | Pieniak | |
| 4,303,189 A | 12/1981 | Wiley et al. | |
| 4,392,862 A | 7/1983 | Marsan et al. | |
| 4,425,127 A | 1/1984 | Suzuki et al. | |
| 4,606,964 A | 8/1986 | Wideman | |
| 4,639,253 A * | 1/1987 | Dyer et al. | 604/362 |
| 4,640,810 A | 2/1987 | Laursen et al. | |
| 4,645,499 A * | 2/1987 | Rupinskas | 604/362 |
| 4,666,647 A | 5/1987 | Enloe et al. | |
| 4,674,966 A | 6/1987 | Johnson et al. | |
| 4,704,112 A | 11/1987 | Suzuki et al. | |
| 4,710,185 A | 12/1987 | Sneyd, Jr. et al. | |
| 4,761,258 A | 8/1988 | Enloe | |
| 4,764,325 A | 8/1988 | Angstadt | |
| 4,765,780 A | 8/1988 | Angstadt | |
| 4,773,903 A | 9/1988 | Weisman et al. | |
| 4,775,579 A | 10/1988 | Hagy et al. | |
| 4,810,568 A | 3/1989 | Buyofsky et al. | |
| 4,834,735 A | 5/1989 | Alemany et al. | |
| 4,837,715 A | 6/1989 | Ungpiyakul et al. | |
| 4,904,440 A | 2/1990 | Angstadt | |
| 4,908,175 A | 3/1990 | Angstadt | |
| 4,915,897 A | 4/1990 | Farrington et al. | |
| 4,915,993 A | 4/1990 | Ten Wolde | |
| 4,927,346 A | 5/1990 | Kaiser et al. | |
| 4,927,582 A | 5/1990 | Bryson | |
| 5,004,579 A | 4/1991 | Wislinski et al. | |
| 5,017,324 A | 5/1991 | Kaiser et al. | |
| 5,124,188 A | 6/1992 | Roe et al. | |
| 5,128,082 A | 7/1992 | Makoui | |
| 5,139,841 A | 8/1992 | Makoui et al. | |
| 5,144,729 A | 9/1992 | Austin et al. | |
| 5,161,283 A | 11/1992 | Hansen | |
| 5,219,633 A | 6/1993 | Sabee | |
| 5,281,208 A | 1/1994 | Thompson et al. | |
| 5,302,445 A | 4/1994 | DePetris et al. | |
| 5,328,072 A | 7/1994 | Ruessmann et al. | |
| 5,334,446 A | 8/1994 | Quantrille et al. | |
| 5,389,095 A | 2/1995 | Suzuki et al. | |
| 5,389,202 A | 2/1995 | Everhart et al. | |
| 5,429,788 A | 7/1995 | Ribble et al. | |
| 5,447,677 A | 9/1995 | Griffoul et al. | |
| 5,466,409 A | 11/1995 | Partridge et al. | |
| 5,486,167 A | 1/1996 | Dragoo et al. | |
| 5,505,720 A | 4/1996 | Walters et al. | |
| 5,514,120 A | 5/1996 | Johnston et al. | |
| 5,527,300 A | 6/1996 | Sauer | |
| 5,531,729 A | 7/1996 | Coles et al. | |
| 5,591,148 A | 1/1997 | McFall et al. | |
| 5,607,415 A | 3/1997 | Datta et al. | |
| 5,614,283 A | 3/1997 | Potnis et al. | |
| 5,622,581 A | 4/1997 | Ducker et al. | |
| 5,672,306 A | 9/1997 | Sprang et al. | |
| 5,704,931 A | 1/1998 | Holtman et al. | |
| 5,756,039 A | 5/1998 | McFall et al. | |
| 5,762,844 A | 6/1998 | Van Himbergen et al. | |
| 5,772,813 A | 6/1998 | Bitowft et al. | |
| 5,803,334 A | 9/1998 | Patel et al. | |
| 5,818,719 A | 10/1998 | Brandon et al. | |
| 5,866,173 A | 2/1999 | Reiter et al. | |
| 5,871,613 A | 2/1999 | Bost et al. | |
| 5,873,963 A | 2/1999 | Trombetta et al. | |
| 5,902,757 A | 5/1999 | Stern et al. | |
| 5,916,661 A | 6/1999 | Benson et al. | |
| 5,925,439 A | 7/1999 | Haubach | |
| 5,938,648 A | 8/1999 | LaVon et al. | |
| 5,944,706 A | 8/1999 | Palumbo et al. | |
| 5,947,945 A | 9/1999 | Cree et al. | |
| 5,961,509 A | 10/1999 | Kling | |
| 5,997,520 A | 12/1999 | Ahr et al. | |
| 6,048,489 A | 4/2000 | Reiter et al. | |
| 6,060,637 A | 5/2000 | Bitowft et al. | |
| 6,090,994 A | 7/2000 | Chen | |
| 6,107,538 A | 8/2000 | Young et al. | |
| 6,203,654 B1 | 3/2001 | McFall et al. | |
| 6,204,207 B1 | 3/2001 | Cederblad et al. | |
| 6,220,999 B1 | 4/2001 | Kugler et al. | |
| 6,258,996 B1 | 7/2001 | Goldman | |
| 6,262,331 B1 | 7/2001 | Nakahata et al. | |
| 6,284,943 B1 | 9/2001 | Osborn, III et al. | |
| 6,296,862 B1 | 10/2001 | Paul et al. | |
| 6,330,735 B1 | 12/2001 | Hahn et al. | |
| 6,375,644 B2 | 4/2002 | Mizutani | |
| 6,416,697 B1 | 7/2002 | Venturino et al. | |
| 6,492,574 B1 | 12/2002 | Chen et al. | |
| 6,533,978 B1 | 3/2003 | Wisneski et al. | |
| 6,533,989 B1 | 3/2003 | Wisneski et al. | |
| 6,575,948 B1 | 6/2003 | Kashiwagi et al. | |
| 6,630,096 B2 | 10/2003 | Venturino et al. | |
| 2001/0027305 A1 | 10/2001 | Raidel et al. | |
| 2001/0039405 A1 | 11/2001 | Keuhn, Jr. et al. | |
| 2003/0116888 A1 | 6/2003 | Rymer et al. | |
| 2003/0119401 A1 | 6/2003 | Chakravarty et al. | |
| 2003/0132556 A1 | 7/2003 | Venturino et al. | |
| 2003/0139721 A1 | 7/2003 | Melius et al. | |
| 2004/0092898 A1 | 5/2004 | Schfer et al. | |
| 2004/0102752 A1 | 5/2004 | Chen et al. | |

FOREIGN PATENT DOCUMENTS

| | | |
|---|---|---|
| DE | 19823954 | 12/1999 |
| EP | 0 151 018 A2 | 8/1985 |
| EP | 0 226 939 A2 | 12/1986 |
| EP | 0 297 180 B1 | 1/1989 |
| EP | 0 298 348 A1 | 11/1989 |
| EP | 0 399 511 A2 | 11/1990 |
| EP | 0 467 409 A1 | 1/1992 |
| FR | 1 535 264 * | 12/1978 |
| GB | 2168612 A | 6/1986 |
| JP | 9122172 | 5/1997 |
| JP | 10211236 | 8/1998 |
| WO | WO 93/18729 A1 | 9/1993 |
| WO | 9600550 | 1/1996 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 00/63479 A1 | 10/2000 |
| WO | WO 01/92003 A1 | 12/2001 |
| WO | WO 03/059232 A2 | 7/2003 |

OTHER PUBLICATIONS

International Search Report, dated Jul. 29, 2003 in PCT/US 03/00294, 3 pages.
International Search Report for PCT/US 03/00293 dated Jul. 29, 2003.
International Search Report for PCT/US 03/01337 dated Jul. 21, 2003.
International Search Report for PCT/US 03/16480 dated Oct. 13, 2003, 5 pages.
International Search Report for PCT/US03/15959 dated Feb. 3, 2004.
International Search Report for PCT/US2004/008428 dated Aug. 23, 2004, 4 pages.
International Search Report for PCT/US2004/006915 dated Nov. 5, 2004, 7 pages.

* cited by examiner

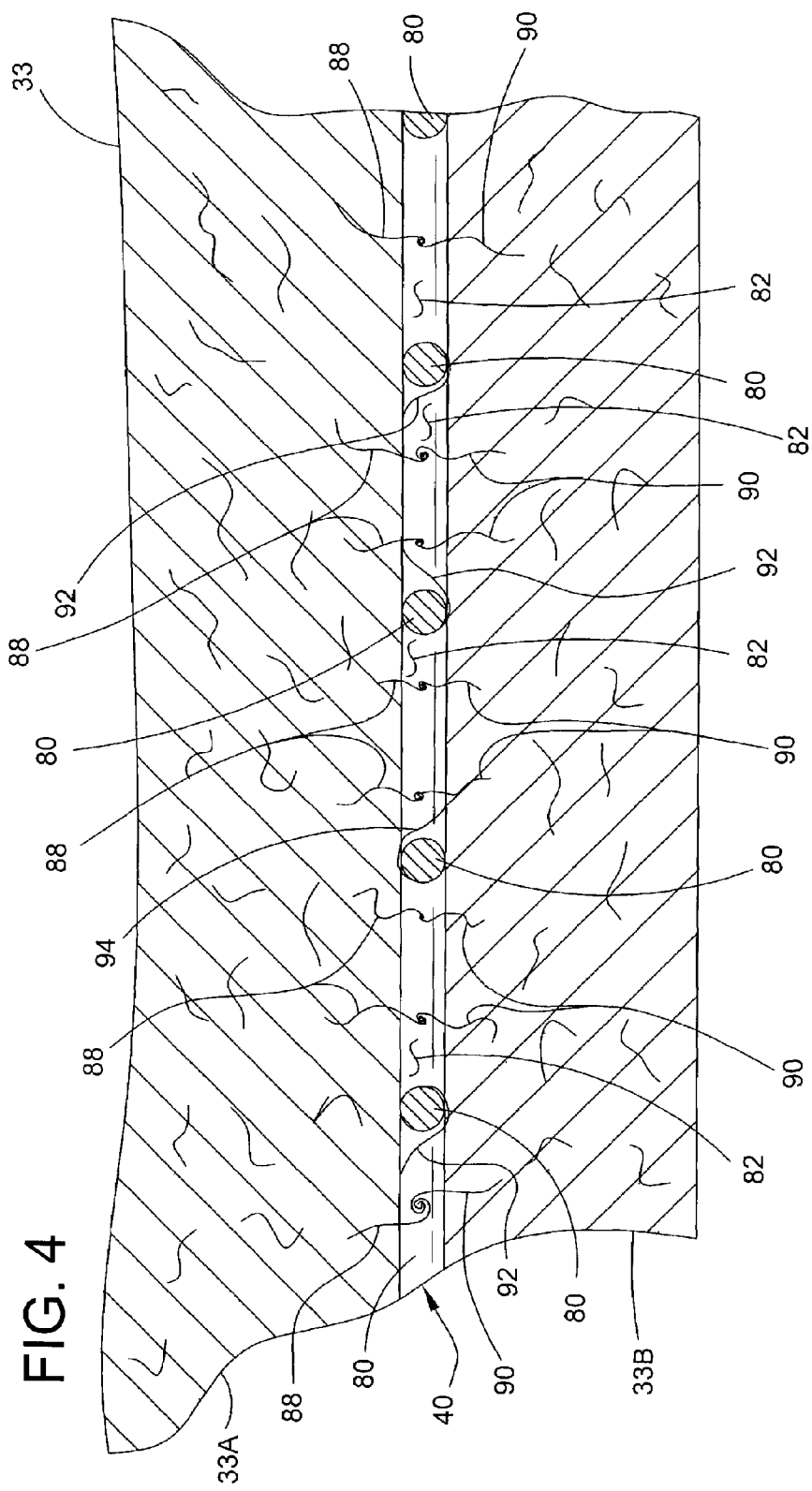

ABSORBENT ARTICLE WITH REINFORCED ABSORBENT STRUCTURE

REFERENCE TO RELATED APPLICATIONS

This is the complete application of and claims priority from provisional application Ser. No. 60/350,079, filed Jan. 15, 2002, entitled "Scrim Reinforced Absorbent."

BACKGROUND OF THE INVENTION

This invention generally relates to an absorbent article and an absorbent structure for such an article. The absorbent structure may include absorbent fibers and a reinforcing member. The reinforced absorbent structure can be employed in absorbent articles, such as disposable diapers, child's training pants, feminine care articles, incontinence articles, bandages, and the like.

Absorbent articles, such as for disposable absorbent garments, may include absorbent structures or cores conventionally formed by air forming or air laying techniques. For example, the manufacture of the absorbent core may begin by fiberizing a fibrous sheet of cellulosic or other suitable absorbent material in a conventional fiberizer, or other shredding or comminuting device, to form discrete fibers. In addition, particles of superabsorbent material are mixed with the discrete fibers. The fibers and superabsorbent particles are then entrained in an air stream and directed to a foraminous forming surface upon which the fibers and superabsorbent particles are deposited to form an absorbent fibrous web. In addition, bonding agents or other strengthening components may be incorporated to provide a more stabilized web.

Other techniques have also been employed to form webs of stabilized absorbent material. Such techniques have included dry-forming techniques, wet-laying techniques, foam-forming techniques, and various wet-forming techniques. The resulting webs of absorbent material have included absorbent fibers, natural fibers, synthetic fibers, superabsorbent materials, binders, and strengthening components in desired combinations. However formed, the absorbent web may then be stored or immediately directed for further processing (e.g., being cut into individual absorbent cores) and assembly with other components to produce a final absorbent article. Absorbent material webs have been strengthened by adding reinforcing members on at least one side of the absorbent material webs. Such reinforcing members have included reinforcement filaments, tissue layers, fabric layers and netting materials. It is also known to add staple binder fibers to the absorbent materials upon formation of the absorbent material web. The binder fibers are activated by heat to produce adhesion of the absorbent materials.

Integrity of an absorbent core formed from such an absorbent material web is desirable to avoid bunching, clumping, cracking and separating of the absorbent core in either a wet or a dry state. This improves the fit and comfort to the wearer of an absorbent article incorporating the absorbent core even as the article receives insults. Sagging and drooping of the absorbent article can cause gaps between the article and the wearer's body which may lead to leaking. As absorbent cores are made both thinner and narrower (particularly in the crotch region), stresses encountered in manufacture and use can be high, requiring reinforcement. In manufacture, tension on the absorbent core can be particularly high during start up and shut down of processing machinery. In use, the lack of integrity can make the absorbent article fit poorly and impact product performance by breaking up the absorbent core, and thereby inhibiting fluid control, liquid handling and wicking which can contribute to leaking.

Co-assigned European Patent Publication No. 0 467 409 A1 discloses one attempt to reinforce an absorbent pad using a scrim material. In that disclosure, a netting or scrim material is used in which some strands have an inner core of one material and an outer sheath of a second material. The scrim is introduced into a forming chamber in which it is incorporated into a fibrous matrix. The second material of the sheath has a lower melting point than the first material of the core. After incorporation of the scrim into the fibrous matrix, the absorbent web formed is heated to melt the sheath for bonding the scrim to the fibers in the matrix. This requires an extra step in the manufacture of a reinforced absorbent.

European Publication No. 0 467 409 also discloses a method for establishing the position of the scrim within the thickness of fibrous matrix. The method does not necessarily require the use of scrim of strands having inner cores and outer sheaths of different material. However, there is no disclosure or suggestion that securing the scrim to the fibrous matrix can be achieved without the use of adhesive and/or fusion bonding.

Conventional reinforcement materials, such as those described above, have exhibited significant shortcomings when employed to form desired absorbent structures. In order to connect the reinforcing member to the surrounding material adhesives and other forms of bonding have been employed which require additional or more complicated manufacturing techniques. Moreover, the conventional reinforcement materials have been expensive, and have had edges that can excessively irritate a wearer's skin. As a result, it has been difficult to provide an absorbent structure that has a desired combination of low-cost, high strength and low irritation. Accordingly, there has been a continued need for an improved technology for providing the desired, reinforced absorbents.

SUMMARY OF THE INVENTION

An absorbent article constructed accordingly to the principles of the present invention can include a matrix of fibers, wherein the fibrous matrix is reinforced with a reinforcing member. The reinforcing member is connected to the fibrous matrix by connections which occur under certain controlled conditions in the manufacture of the absorbent core. No additional securing steps are required. In another aspect, the reinforcing member can be restricted to a longitudinally extending, medial region of the absorbent structure. In a particular arrangement, the reinforcing member can have a cross-directional width dimension which is less than a narrowest width dimension of the fibrous matrix. In a further aspect, the reinforcing member material can be located at any desired location within the thickness (i.e., "z-direction") of the absorbent core.

By incorporating the various aspects and features into desired configurations, the present invention can provide an article that more effectively incorporates a reinforced absorbent structure. The invention can produce an article having a high-strength absorbent structure that can provide reduced irritation to the wearer, and can be constructed at reduced cost.

In one aspect of the invention, an absorbent structure for absorbing liquid comprises an absorbent member including an upper region and a lower region, each at least partially made of fibers. A reinforcing member located between the upper region and the lower region maintains the structural integrity of the absorbent member. The reinforcing member is permeated by fibers from the upper region to the lower region and from the lower region to the upper region, at least some of the permeating fibers from each of the upper and lower regions being entangled with fibers in the other of the upper and lower regions to facilitate interconnection of the upper and lower regions and the reinforcing member.

In another aspect of the present invention, an absorbent article comprises a liquid permeable liner, a backsheet layer and an absorbent structure as set forth in the preceding paragraph, which is disposed between the liner and the backsheet layer.

In a further aspect, an absorbent structure for absorbing liquid comprises an absorbent member including fibers, and a reinforcing member for maintaining the structural integrity of the absorbent member. The reinforcing member is permeated by fibers from the absorbent member and has openings therein. At least some of the permeating fibers project through the openings in the reinforcing member and are entangled with the reinforcing member.

In a still further aspect of the present invention, an absorbent structure for absorbing liquid comprises an absorbent member including fibers and a reinforcing member. The reinforcing member is substantially free of attachment to the absorbent structure except through at least one of entanglement of the fibers with the reinforcing member; entanglement of fibers with other fibers entangled with the reinforcing member and entanglement of fibers with each other where at least one of the entangled fibers passes through the reinforcing member.

In another aspect of the present invention, an absorbent article adapted to be worn generally at the lower torso to capture body exudates comprises a liquid permeable liner, a backsheet layer and an absorbent structure disposed between the liner and the backsheet layer. The absorbent structure comprises an absorbent core including fibers and reinforcing scrim. The scrim is connected to the fibers by entanglement of the fibers with the scrim, entanglement of fibers with other fibers entangled with the scrim and entanglement of fibers with each other where at least one of the entangled fibers passes through the scrim.

Other features of the invention will be in part apparent and in part pointed out hereinafter.

BRIEF DESCRIPTION OF THE DRAWINGS

FIG. 4 is a further enlarged, fragmentary, longitudinal section of the absorbent core of the absorbent article showing a reinforcing member and schematically illustrating the interconnection of fibers of the absorbent core with each other and the reinforcing member;

Corresponding reference characters indicate corresponding parts throughout the several views of the drawings.

DETAILED DESCRIPTION OF THE DRAWINGS

The technology of the invention can be configured to produce various types of desired absorbent articles. Such articles can include, for example, infant diapers, children's training pants, feminine care articles, adult incontinence garments, bandages and the like for use in absorbing various body exudates. The articles may be, but are not necessarily, disposable, and intended for limited use. Typically, the disposable articles are not intended for washing and reuse.

Figure 1:
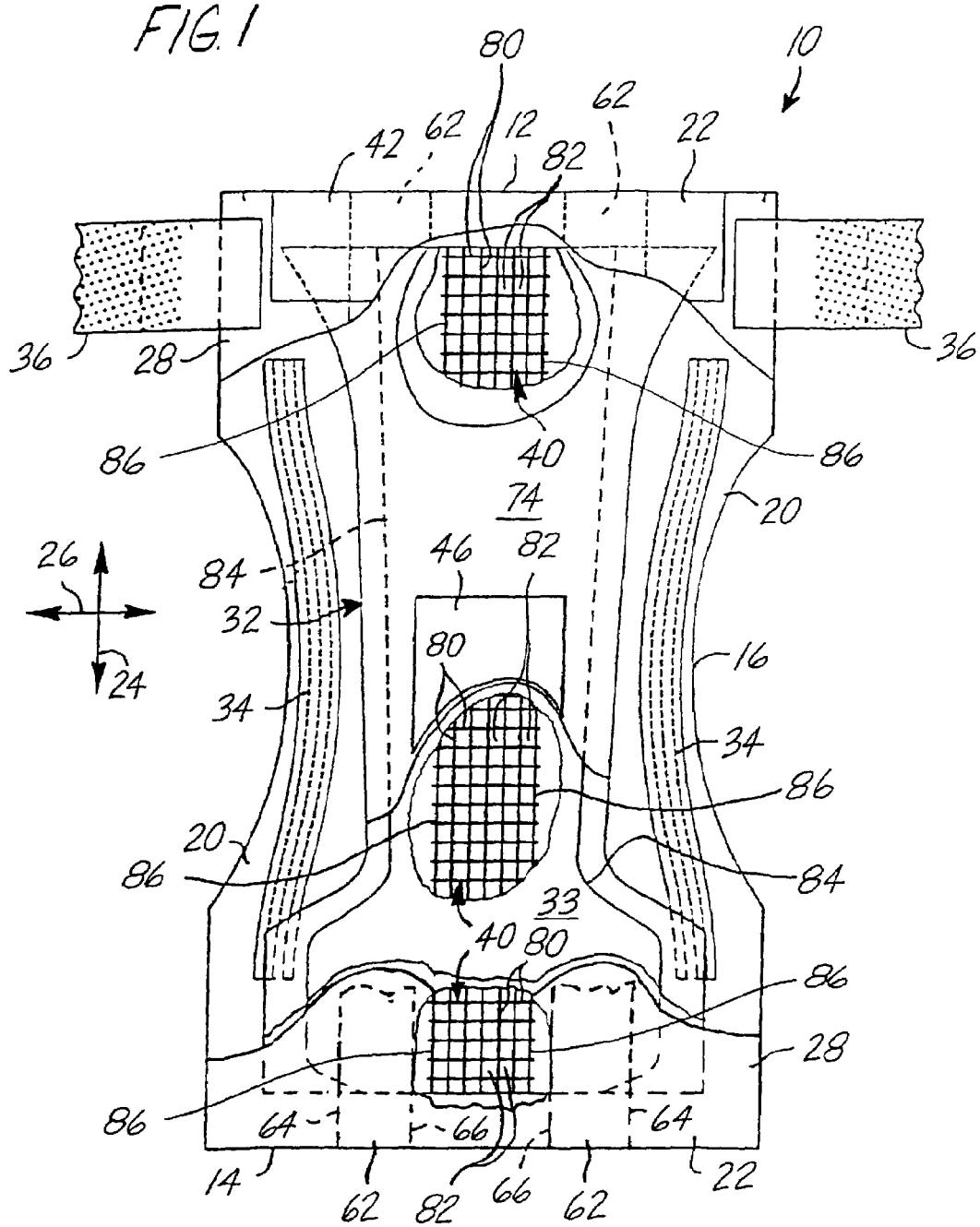
FIG. 1 is a top plan view of an absorbent article with parts broken away to show internal construction.
Figure 2:
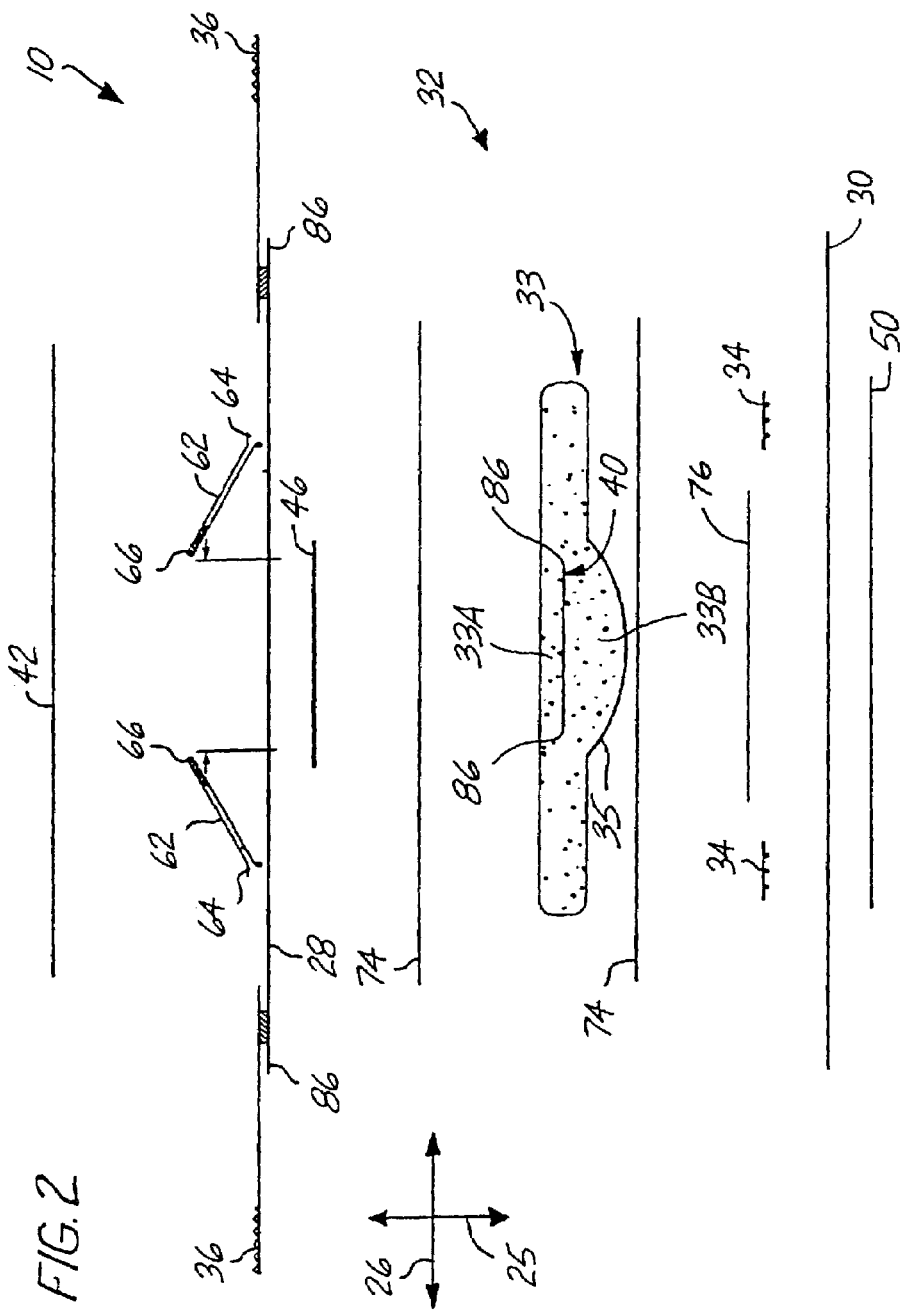
FIG. 2 is a schematic, exploded view, in cross-section, of an absorbent article that incorporates the present invention.

Referring now to the drawings, and in particular to FIGS. 1 and 2, an absorbent article constructed according to the principles of the present invention is shown in the form of a diaper 10 unfolded and laid flat with substantially all elastic induced gathering and contraction removed. The diaper 10 extends lengthwise in a longitudinal or machine-direction 24, widthwise in a lateral or cross-direction 26, and has a thickness in a "z" or thickness direction 25. For the purposes of the present disclosure, the machine-direction 24 lies generally parallel to the plane of the diaper 10, and extends generally along a line that lies between opposed end regions of the diaper. The cross-direction 26 lies generally parallel to the plane of the article, and is aligned perpendicular to the longitudinal-direction 24. The z-direction 25 is aligned substantially perpendicular to both the longitudinal-direction 24 and the cross-direction 26, and extends through the thickness of the diaper 10. In FIG. 1, the bodyside surface of the diaper which contacts the wearer is facing the viewer and, portions of the structure are partially cut away to more clearly show the interior construction of the diaper article 10. The outer edges of the diaper define a periphery with longitudinally extending side edge margins 20 and laterally extending end edge margins 22. The side edges define leg openings for the diaper 10.

With regard to the designated surfaces of the article, the various inward or bodyside surfaces are configured to face toward the body of the wearer when the article is placed about the wearer. The designated outward surfaces of the article are configured to face away from the wearer's body when the article is placed about the wearer. The diaper 10 may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The diaper 10 includes an absorbent structure, generally indicated at 32, having an absorbent core 33 (broadly, "an absorbent member") which includes absorbent fibers and superabsorbent material (SAM). The absorbent core 33 may also include other fibers which are not absorbent. A web of scrim 40 (broadly, "a reinforcing member") is located roughly in the middle of the absorbent core 33 for reinforcing the fibrous absorbent core to enhance the integrity of the core under loads as will be described more fully hereinafter. The actual position of the scrim between major surfaces of the core 33 various over the core because in the illustrated embodiment, the core has a non-constant thickness. It is to be understood that the scrim can be placed away from the middle, toward one side or the other within the absorbent core thickness and still fall within the scope of the invention. A backsheet layer 30 and a liquid permeable topsheet layer 28 are arranged opposite each other and the absorbent structure 32 is located between the backsheet layer and topsheet layer. Typically, the backsheet layer 30 is liquid impermeable, but may be liquid permeable without departing from the scope of the present invention. The illustrated diaper 10 has a first or back waistband portion 12, a second or front waistband portion 14 and an intermediate or crotch portion 16 that interconnects the back and front waistband portions. In use, the diaper 10 is fitted onto the lower torso and around the upper legs of a wearer (e.g., a child or infant), assuming a curved, three dimensional configuration in which parts of the back and front waistbands portions 12, 14 overlie or lie in close proximity to each other.

A fastening system including fastener tabs 36 and a landing zone patch 50 for receiving the fastener tabs to interconnect the back waistband portion 12 with the front waistband portion 14 to hold the article on a wearer so that the back portion overlaps the front portion. However, a fastening system (not shown) could be used in which a front waistband portion overlaps the back waistband portion. In such optional arrangements, the front waistband portion would be the "first" waistband portion and the back waistband region would be the "second" waistband portion. The diaper also has a system of elastomeric gathering members, including leg elastics 34 to draw the diaper 10 around the legs and a waist elastic 42 (located in the back waistband portion 12) to draw the diaper around the waist.

The backsheet layer 30 is located along an outside surface of the absorbent structure 32 and may be composed of a liquid permeable material, but desirably comprises a material which is configured to be substantially impermeable to liquids. For example, a typical backsheet layer 30 can be manufactured from a thin plastic film, or other flexible, substantially liquid-impermeable material. As used in the present disclosure, the term "flexible" refers to materials which are compliant and which will readily conform to the general shape and contours of the wearer's body. The backsheet layer 30 can prevent the exudates contained in absorbent structure 32 from wetting articles, such as bedsheets and overgarments, which contact diaper 10. In particular embodiments of the invention, backsheet layer 30 can include a film, such as a polyethylene film, having a thickness of from about 0.012 millimeters (0.5 mil) to about 0.051 millimeters (2.0 mil). For example, the backsheet film can have a thickness of about 0.032 millimeters (1.25 mil).

Alternative constructions of the backsheet layer 30 may comprise a woven or non-woven fibrous web which has been totally or partially constructed or treated to impart the desired levels of liquid impermeability to selected regions that are adjacent or proximate the absorbent structure. For example, the backsheet layer 30 may include a gas-permeable, non-woven fabric material laminated to a facing surface of a polymer film material that may or may not be gas-permeable. Ordinarily, the fabric material is attached to an outward-facing surface of the polymer film material. Other examples of fibrous, cloth-like backsheet layer materials are a stretch-thinned or a stretch-thermal-laminate material composed of a 0.015 mm (0.6 mil) thick polypropylene blown film and a 23.8 g/m$^2$ (0.7 osy) polypropylene spunbond material (2 denier fibers).

In particular arrangements, a substantially liquid impermeable, vapor permeable backsheet layer 30 may be a composite material which includes a vapor permeable film adhesively laminated to a spunbond material. The vapor permeable film can be obtained from Exxon Chemical Products Incorporated, under the tradename EXXAIRE. The film can include 48-60 weight percent (wt %) linear low density polyethylene and 38-50 wt % calcium carbonate particulates that may be uniformly dispersed and extruded into the film. The stretched film can have a thickness of about 0.018 mm (0.7 mil) and a basis weight of 16-22 g/m$^2$. The spunbond material can be adhesively laminated to the film, and can have a basis weight of about 27 g/m$^2$. The spunbond material can be made using conventional spunbond technology, and can include filaments of polypropylene having a fiber denier of 1.5-3 dpf. The vapor-permeable film may be adhered to the spunbond material using a pressure sensitive, hot melt adhesive at an add-on rate of about 1.6 g/m$^2$, and the adhesive can be deposited in the form of a pattern of adhesive swirls or a random fine fiber spray. Another example of a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

The liquid impermeable, vapor permeable backsheet layer 30 may alternatively include a highly breathable stretch thermal laminate material (HBSTL). The HBSTL material can include a polypropylene spunbond material thermally attached to a stretched breathable film. For example, the HBSTL material may include a 20.4 g/m$^2$ (0.6 osy) polypropylene spunbond material thermally attached to an 18.7 g/m$^2$ stretched breathable film. The breathable film may include two skin layers with each skin layer composed of 1-3 wt % EVA/catalloy. The breathable film may also include 55-60 wt % calcium carbonate particulates, linear low density polyethylene, and up to 4.8% low density polyethylene. The stretched breathable film can include a thickness of 0.011-0.013 mm (0.45-0.50 mils) and a basis weight of 18.7 g/m$^2$. The spunbond material can be thermally bonded to the breathable film, and can have a basis weight of about 20.4 g/m$^2$. The spunbond material can have a fiber denier of 1.5-3 dpf, and the stretched breathable film can be thermally attached to the spunbond material using a "C-star" pattern that provides an overall bond area of 15-20%.

The various types of such materials have been employed to form the backsheet layer or outer cover of disposable diapers, such as HUGGIES disposable diapers which are commercially available from Kimberly-Clark Corporation. Optionally, however, the article may include a separate component that is additional to the backsheet layer. The backsheet layer 30 may also be embossed or otherwise provided with a pattern or matte finish to exhibit a more aesthetically pleasing appearance.

The topsheet layer 28 presents a body-facing surface that is compliant, soft-feeling, and non-irritating to the wearer's skin. Further, the topsheet layer 28 can be less hydrophilic than absorbent structure 32, and is sufficiently porous to be liquid permeable, permitting liquid to readily penetrate through its thickness to reach the absorbent structure. A suitable topsheet layer 28 may be manufactured from a wide selection of materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent structure 32. Various woven and nonwoven fabrics can be used for topsheet layer 28. For example, the topsheet layer may be composed of a meltblown or spunbonded web of the desired fibers, and may also be a bonded-carded-web. The various fabrics can be composed of natural fibers, synthetic fibers or combinations thereof. For the purposes of the present description, the term "nonwoven web" means a web of fibrous material that is formed without the aid of a textile weaving or knitting process. The term "fabrics" is used to refer to all of the woven, knitted and nonwoven fibrous webs.

The topsheet layer fabrics may be composed of a substantially hydrophobic material, and the hydrophobic material may optionally be treated with a surfactant or otherwise processed to impart a desired level of wettability and hydrophilicity. In a particular embodiment of the invention, topsheet layer 28 is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% TRITON X-102 surfactant. Other types and amounts of operative surfactants may alternatively be employed. The surfactant can be applied by any conventional means, such as spraying, printing, brush coating or the like.

The topsheet layer 28 and backsheet layer 30 are connected or otherwise associated together in a suitable manner. As used herein, the term "associated" encompasses configurations in which topsheet layer 28 is directly joined to backsheet layer 30 by affixing topsheet layer directly to backsheet layer, and configurations wherein topsheet layer is indirectly joined to backsheet layer by affixing topsheet layer to intermediate members which in turn are affixed to backsheet layer. The topsheet layer 28 and backsheet layer 30 can, for example, be joined to each other in at least a portion of the diaper periphery in a suitable manner such as by adhesive bonding, sonic bonding, thermal bonding, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet layer to the backsheet layer. It should be readily appreciated that the above-described attachment mechanisms may also be employed to suitably interconnect, assemble and/or affix together the various other component parts of the articles that are described herein.

The diaper 10 also includes a surge management member 46 which helps to decelerate and diffuse surges or gushes of liquid that may be rapidly introduced into the absorbent structure of the article. Desirably, the surge management member 46 can rapidly accept and temporarily hold the liquid prior to releasing the liquid into the absorbent structure 32. In the illustrated embodiment, for example, the surge member 46 is located on an inwardly facing body side surface of the topsheet layer 28. Alternatively, the surge member 46 may be located adjacent to an outer side surface of the topsheet layer 28. Accordingly, the surge member 46 is interposed between the topsheet layer 28 and the absorbent structure 32. Examples of suitable surge management members 46 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996; and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996; the entire disclosures of which are hereby incorporated by reference. However, it is to be understood that the surge management member 46 can be omitted without departing from the scope of the present invention.

Elasticized containment flaps 62 extend generally lengthwise in the machine-direction 24 of the diaper 10. The containment flaps 62 are typically positioned laterally inboard from the leg elastics 34, and substantially symmetrically placed on each side of the longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 entitled DIAPERS WITH ELASTICIZED SIDE POCKETS by K. Enloe which issued Nov. 3, 1987, the entire disclosure of which is hereby incorporated by reference. The containment flaps 62 may be composed of a wettable or a non-wettable material, as desired. In addition, the containment flap material may be substantially liquid-impermeable, may be permeable to only gas or may be permeable to both gas and liquid. The level of permeability of the containment flap material may be substantially the same as or different than the permeability of other components of the article. Other suitable containment flap configurations are described in U.S. Pat. No. 5,562,650 entitled ABSORBENT ARTICLE HAVING AN IMPROVED SURGE MANAGEMENT by R. Everett et al., which issued Feb. 13, 1996, the disclosure of which is hereby incorporated by reference.

In optional, alternative configurations of the invention, diaper 10 may include internal, elasticized, containment waist flaps, such as those described in U.S. Pat. No. 4,753,646 entitled DIAPER WITH WAIST FLAPS by K. Enloe which issued Jun. 28, 1988; and in U.S. Pat. No. 5,904,675 entitled AN ABSORBENT ARTICLE WITH IMPROVED ELASTIC MARGINS AND CONTAINMENT SYSTEM by D. Laux et al., which issued May 18, 1999; the entire disclosures of which are hereby incorporated by reference. Similar to the construction of the containment flaps 62, the containment waist flaps may be composed of a wettable or non-wettable material, as desired. The waist flap material may be substantially liquid-impermeable, permeable to only gas, or permeable to both gas and liquid.

The landing zone patch 50 provides a target area for releasable and re-attachable securement with the fastener tabs 36. The landing zone patch 50 is positioned on the front waistband portion 14 of the diaper 10 and located on the outward surface of the backsheet layer 30 in the illustrated embodiment. Alternatively, the landing zone patch 50 could be positioned on an inward surface of the diaper 10, such as the bodyside surface of the topsheet layer 28, or at any other suitable location. Particular arrangements of the invention can include one or more landing members that can be directly or indirectly attached to the second waistband portion 14. The landing zone patch 50 can be composed of a substantially non-elastomeric material, such as polymer films or tapes, woven fabrics, nonwoven fabrics or the like, as well as combinations thereof. The landing zone patch 50 could also be made of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 26.

The fastener tabs 36 are located at rearward portions of the side edges 20 near the back waistband portion 12, but could be located at front portions of the side edges near the front waistband portion 14. The fastener tab 36 can be made of a substantially non-elastomeric material, such as polymer films or tapes, woven fabrics, nonwoven fabrics or the like, as well as combinations thereof. Optionally, the fastener tabs 36 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least in the lateral direction 26.

In the various aspects and configurations of the invention, the fastening mechanism between the selected first fastener component and the selected, second fastener component may be adhesive, cohesive, mechanical or combinations thereof. In the context of the present invention, a mechanical fastening system is a system that includes cooperating, first and second components that mechanically interengage to provide a desired securement. Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated embodiment, the mechanical fastening system is of the hook-and-loop type. Such fastening systems typically include attachment members having the form of a "hook" or hook-like, male component, and include a cooperating "loop" or loop-like, female component that engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners. As illustrated, the hook element is located on the fastener tab 36 and the loop element on the patch 50, but the arrangement of the hook element and the loop element could be reversed.

The absorbent structure 32 has a construction that is generally compressible, conformable, non-irritating to the wearer's skin, and capable of absorbing and retaining body exudates. It should be understood that, for purposes of this invention, the absorbent structure 32 comprises several parts that are assembled together. The absorbent core 33 of the absorbent structure 32 may be constructed of any of a number of absorbent materials, as are well known in the art. For example, the absorbent core 33 may be provided by a layer of coform, meltblown fibers, bonded carded webs, a wetlaid body, tissue laminates, foams, a surge/air formed composite and the like or combinations thereof. In particular, the absorbent core 33 may be provided as a combination of hydrophilic fibers, and high-absorbency material.

In the illustrated embodiment, the absorbent core 33 is zoned, having a selected zone 35 of higher basis weight (FIG. 2). There may be multiple zones or portions of the absorbent core selected to have particular properties. In the illustrated embodiment the zone 35 is constructed and arranged to provide for additional retention of liquid (as compared to the other regions of the core 33). The zone 35 may be positioned in a location where maximum absorbent capacity is needed. Descriptions of ways to form zoned absorbent cores are disclosed in co-assigned U.S. Pat. No. 4,761,258 entitled CONTROLLED FORMATION OF LIGHT AND HEAVY FLUFF ZONES by K. Enloe which issued Aug. 2, 1988; U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001; and U.S. patent application Ser. No. 10/207,929 entitled APPARATUS AND FORM FOR MAKING AN AIR FORMED FIBROUS WEB by Venturino et al., filed Jul. 30, 2002, the disclosures of which are incorporated by reference.

Various types of wettable, hydrophilic fibrous material can be used to provide the fiber material for the absorbent core 33. Examples of suitable fibers include naturally occurring organic fibers composed of intrinsically wettable material, such as cellulosic fibers including wood pulp fibers which can be curled, crosslinked or otherwise mechanically or chemically modified. Other examples of suitable fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The high-absorbency material used in the absorbent core 33 may comprise absorbent gelling materials, such as superabsorbent materials. Absorbent gelling materials can be natural, biodegradable, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

The high-absorbency material used in the absorbent core 33 is generally in the form of discrete particles. The particles can be of any desired shape, for example, spiral or semispiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent core 33. Desired for use are particles having an average size of from about 20 micrometers to about 1 millimeter. "Particle size" as used herein means the weighted average of the smallest dimension of the individual particles.

The absorbent materials and superabsorbent materials may be integrated into the absorbent core by employing any operative method or apparatus. For example, the absorbent core may be formed with a dry-forming technique, an air forming technique, a wet-forming technique, a foam-forming technique or the like, as well as combinations thereof. Certain methods and apparatus for carrying out such techniques are well known in the art. One example is described more fully below in reference to FIG. 7.

The web of scrim 40 is incorporated into the absorbent core 33 of the absorbent structure 32. In an embodiment illustrated in FIGS. 1-4, the scrim 40 comprises elongate strands 80 which are arranged so that the strands intersect each other. More specifically, the strands 80 are arranged in a grid including parallel strands extending in the machine-direction 24 and strands extending in the cross-direction 26 defining rectangular openings 82 in the scrim. Among other things, the openings 82 permit liquid in the absorbent core 33 to flow substantially unhindered through the scrim 40. The strands 80 are secured to each other where they intersect to create a lattice providing strength and stability to the absorbent core. In one embodiment, the width of the scrim 40 is equal to the minimum width of the absorbent core 33 (usually located at the portion of the core which is worn through the crotch). In other embodiments, the width of the scrim 40 is between 25% and 100% and more preferably between 50% and 100% of the narrowest width dimension of the absorbent core 33.

The scrim 40 can be made of any suitable material that provides desired levels of strength and flexibility. For example, the strands 80 of the scrim 40 may be composed of natural or synthetic materials, as well as combinations thereof. In a particular arrangement, the material of the strands 80 may include a synthetic polymer (e.g., polyester, polyethylene, polypropylene, nylon, rayon). The synthetic polymer may be monofilament, bicomponent or multicomponent. One conventional way to form scrim of such material is to extrude and orient strands to form a net configuration. Another way of forming such material is by a photomasking process. In that process, a photosensitive resin is deposited on a woven fabric. A mask is applied in the form of the scrim and electromagnetic radiation is used to cure the unmasked portions of the resin. The mask is then removed and the uncured portions of the resin are washed away, leaving the scrim-patterned, cured resin. Natural materials that could be used to form the scrim include cotton, jute, hemp, wool. Alternate materials include glass, carbon and metallic fibers. The reinforcing scrim 40 can be a woven or nonwoven material. The scrim strands in the machine-direction 24 and cross direction 26 could be of different materials. Alternately different materials could be used in alternating scrim strands in the machine-direction and/or cross-direction. In one embodiment, the strands 80 may be formed of superabsorbent material. In that event, the scrim 40 would serve a liquid retention function in addition to its reinforcing function. Still further, the scrim 40 could be formed of one material and coated with another material, or be a biodegradable material, such as polylactic acid. An example of a superabsorbent coating is given in co-assigned application Ser. No. 10/246,811 entitled ABSORBENT ARTICLES HAVING A SUPERABSORBENT RETENTION WEB by Newbill et al., filed Sep. 18, 2002, the disclosure of which is incorporated herein by reference.

A suitable scrim material is RO3230 Polypropylene Scrim material available from Conwed Plastics, a business having offices in Minneapolis, Minn., U.S.A. The selected scrim was for a diaper application. It will be understood that for a feminine hygiene product or an adult incontinence product, a scrim with different physical properties would likely be selected to best meet the needs of the users of those products. Diapers having absorbent cores incorporating scrim RO3230 were tested and found not to be significantly stiffer than similar, unreinforced diapers. The tests are performed by placing a folded diaper in a fixture (not shown) so that the diaper rests on edge in a generally "V" shape (the angle between halves of the diaper being roughly 90 degrees). The diaper is then compressed edgewise to 50% of its original height and the force required to produce this compression of the diaper is read. As previously noted, the results found no significant differences in stiffness between conventional diapers without reinforcing scrim and those with scrim.

The position in the z-direction 25 of the scrim 40 within the absorbent core may be selectively changed. The scrim 40 is shown extending the full length of the absorbent core 33, but may have a lesser or greater length without departing from the scope of the present invention. The absorbent core 33 has longitudinal edges 84. The scrim 40 is narrower than the absorbent core 33 and arranged so that its longitudinal edges 86 are everywhere located inward of the longitudinal edges 84. In this way, longitudinal edges 86 of the scrim 40 are embedded in and shielded by the fibrous material of the absorbent core 33 so that they do not irritate the skin or abrade or poke holes in other parts of the diaper 10. It is noted that the core 33 is partially broken away in FIG. 1, but extends continuously over its length and embeds the scrim 40. It has been found that the scrim 40 may help the absorbent core 33 hold its shape in conformance with the wearer's body thereby improving fit and increasing comfort. However, it is to be understood that scrim (not shown) which extends laterally beyond one or both of the longitudinal edges of the absorbent core or structure may also be used.

In the illustrated embodiment, the scrim 40 defines a boundary area between the upper and lower regions 33A, 33B. Because the scrim 40 is narrower than the absorbent core 33, the upper and lower regions 33A, 33B have no dividing boundary area and are not distinct away from the scrim. The scrim 40 may be incorporated in the absorbent core 33 in a suitable manner, such as during the formation of the absorbent core. Suitable air forming methods and apparatus for such incorporation are disclosed in co-assigned U.S. patent application Ser. No. 10/306,269, entitled PROCESS AND APPARATUS FOR MAKING A REINFORCED FIBROUS ABSORBENT MEMBER, by Venturino et al. and Ser. No.

10/305,755, entitled PROCESS AND APPARATUS FOR AIR FORMING AN ARTICLE HAVING A PLURALITY OF REINFORCED SUPERIMPOSED FIBROUS LAYERS, by Heyn et al., and Ser. No. 10/306,186, (now U.S. Pat. No. 6,981,297) entitled CONTROLLED PLACEMENT OF A REINFORCING WEB WITHIN A FIBROUS ABSORBENT by Venturino et al., filed simultaneously herewith, the disclosures of which are incorporated herein by reference. It is noted that these forming methods and apparatus promote the entanglement of the fibers with the scrim 40 and with each other during manufacture of the absorbent core 33. However, post-formation entanglement such as by needle punching or hydroentangling may be used to augment the connection. It is also believed that entanglement is augmented by passing the fibrous web of material containing the scrim through a nip or other debulking device, as described below.

Figure 3:
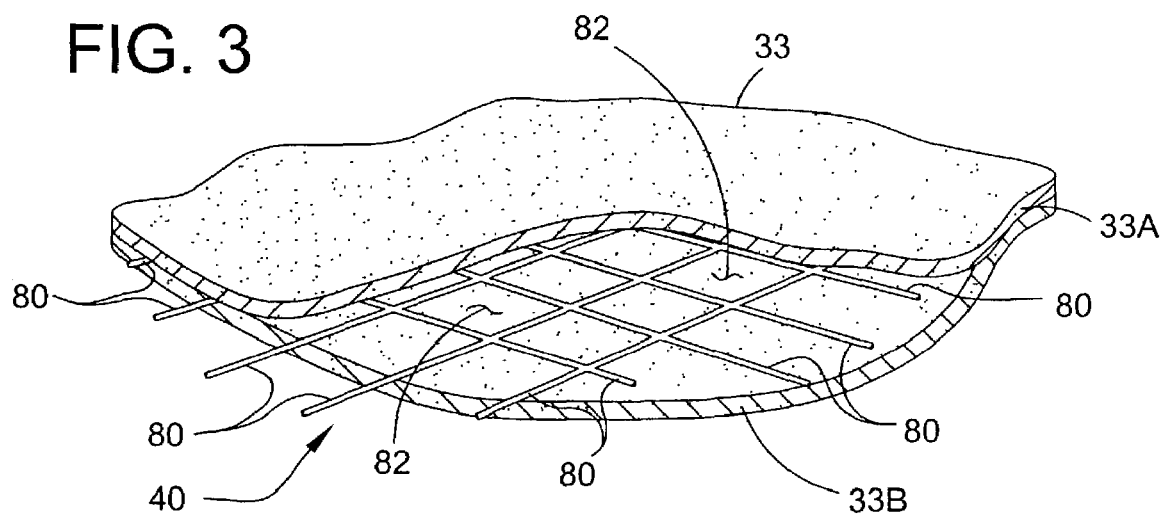
FIG. 3 is a greatly enlarged, fragmentary schematic perspective of an absorbent core with parts broken away to show internal construction.

The interconnection of the upper and lower regions 33A, 33B and the scrim 40 is illustrated in FIGS. 3 and 4. These drawings schematically illustrate the mechanical connections made between the upper region 33A and the lower region 33B, and between both of those regions and scrim 40. At least some fibers 88 from the upper region 33A pass through openings 82 in the scrim 40 and are entangled with fibers 90 from the lower region 33B. In the same way, at least some of the fibers 90 from the lower region 33B pass through the openings 82 in the scrim 40 and are entangled with fibers 88 in the upper region 33A. Thus, the upper and lower regions 33A, 33B are connected to each other by fiber entanglement through the scrim 40. In addition, at least some fibers 92 from the upper region 33A and at least some fibers 94 from the lower region 33B are entangled with the strands 80 of the scrim 40 itself so that mechanical connection is also made with the scrim. In this way, there is a strong joining of the upper and lower regions 33A, 33B to each other and with the scrim 40 so that the scrim can reinforce the upper and lower regions substantially free of any adhesive, fusion or other connection to the absorbent core 33 other than at least one of: entanglement of the fibers with the scrim; entanglement of fibers with fibers entangled with the scrim; and entanglement of fibers with each other where at least one of the fibers passes through the scrim. It is recognized that certain processing steps, e.g., debulking, may producing some additional connection between the scrim 40 and fibers of the absorbent core 33, such as by way of hydrogen bonding. For purposes of the present description, such connections do not detract from the connection of the scrim 40 with the fibers of the absorbent core 33 being substantially free of connection other than through entanglement. The absorbent structure of the present invention, at least in one embodiment, does not require the use of an adhesive to bond the scrim 40 with the fibers of the core 33 and does not require fusion of the scrim with the fibers to produce a robust and durable absorbent core.

In use, the scrim 40 holds the matrix of the fibrous material in the absorbent core 33 together against loads applied through movement of the wearer and by liquid in the absorbent core 33 after receiving one or more insults. These loads tend to cause the fibrous material (and hence the absorbent core 33) to tear apart. The scrim 40 resists forces applied to the absorbent core 33 such as but not limited to tensile, compressive, and shear. The scrim 40 allows the absorbent core 33 to have a lower basis weight of fibrous material because of the additional strength. Accordingly, the construction of a thinner absorbent core 33 and a thinner absorbent structure 32 is facilitated.

Figure 5A:
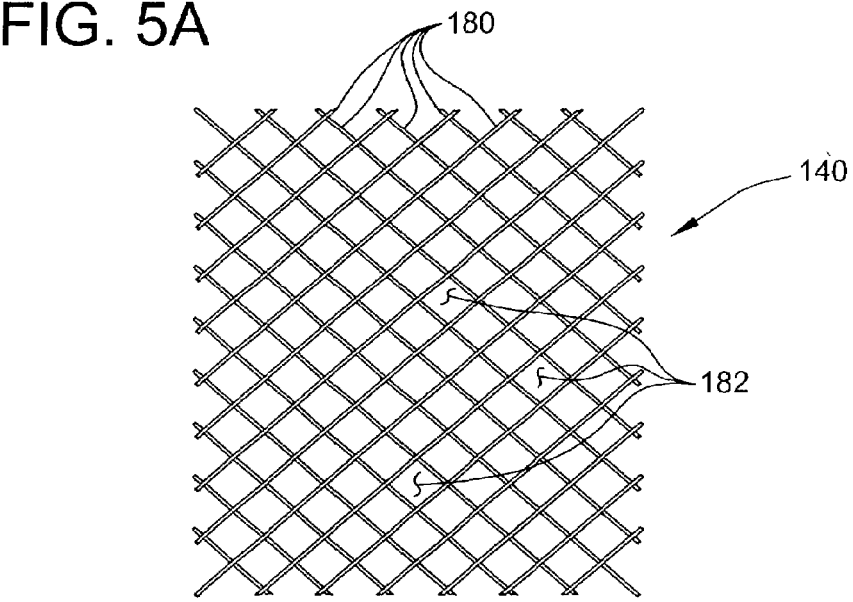
FIG. 5A is a plan view of a reinforcing member in the form of scrim material having diamond shaped openings.
Figure 5B:
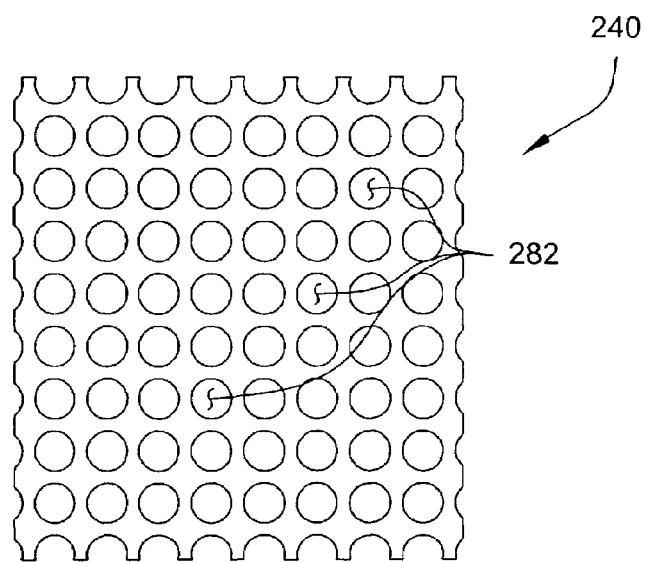
FIG. 5B is a plan view of a reinforcing member in the form of apertured sheet material.

FIGS. 1-4 illustrate one form of reinforcing member in the form of scrim 40 composed of strands 80 which intersect each other in a regular fashion and form rectangular openings 82. However, the reinforcing member need not have rectangular openings nor be composed of a lattice of strands 80. Referring to FIG. 5A, the reinforcing member is shown in the form of scrim 140 composed of strands 180 intersecting one another to form diamond-shaped openings 182. However, the strands 180 could be arranged for defining openings of still other shapes, including openings defined by non-linearly arranged strands and openings within the same scrim having different shapes (not shown). FIG. 5B shows the reinforcing member in the form of sheet material, such as a film 240 having openings 282 formed therein for extension of fibers from the upper and lower fibrous regions (not shown, but like regions 33A, 33B) through the film and around the film between openings for the same secure interconnection of the component parts of the absorbent structure. The film 240 may be formed, among other ways, by perforating a continuous film, or by cast film technology in which a polymer material is applied to a drum having raised portions which form openings and/or other features in the cast polymer material. In still another possible embodiment (not shown), the reinforcing member is spunbond material formed prior to the manufacture of the absorbent structure and fed into the absorbent structure manufacturing apparatus from a roll. The spunbond material has irregular openings which perform the same function as the openings (82,182,282) of the embodiments of FIGS. 3, 4, 5A and 5B.

Figure 6A:
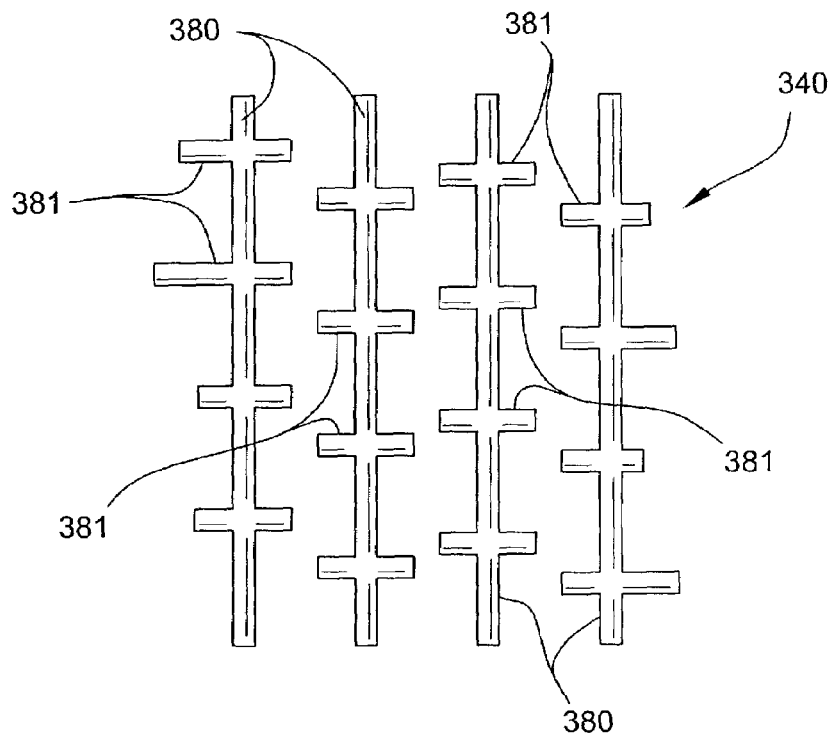
FIG. 6A is a plan view of a reinforcing member in the form of separate elongate strands having perpendicular cross pieces.

The reinforcing member may take the form of several components which are unconnected to each other except through their common connection to the absorbent core. For instance, the reinforcing member could be two or more separate webs or pieces of scrim (not shown). In one example, laterally spaced pieces of scrim may extend continuously lengthwise of the absorbent core. Another type of reinforcing member including discontinuous components is illustrated in FIGS. 6A-6D. Referring to FIG. 6A, the reinforcing member 340 may take the form of one or more spaced apart strands 380 which are unconnected to each other in the absorbent core except through connection with the upper and lower regions. The absorbent core is not illustrated in FIGS. 6A-6D for clarity in showing the reinforcing members. These embodiments have a reduced resistance to tearing forces in directions lateral of the absorbent core, but are constructed to resist longitudinal tearing forces.

Figure 6B:
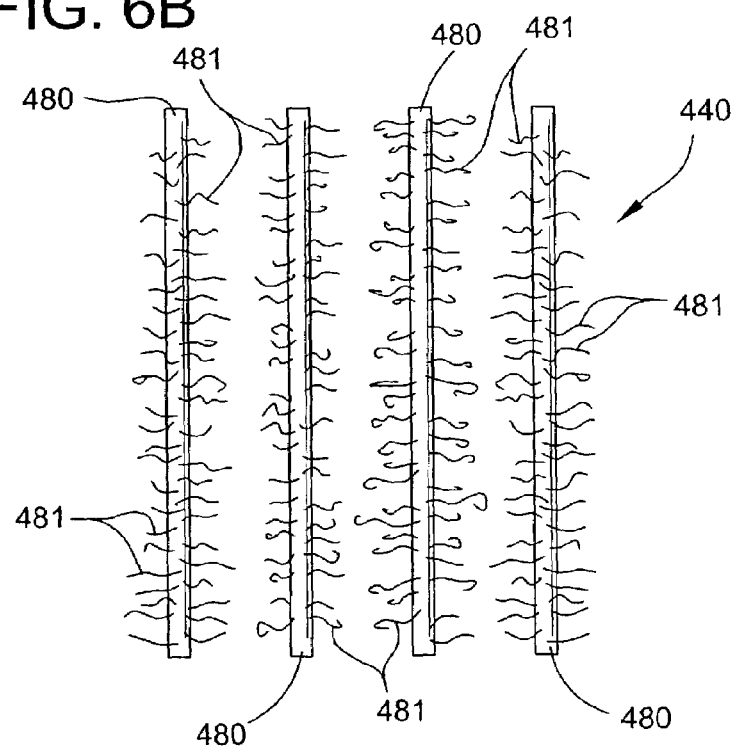
FIG. 6B is a plan view of a reinforcing member in the form of separate elongate strands having small diameter filaments projecting outwardly therefrom.
Figure 6C:
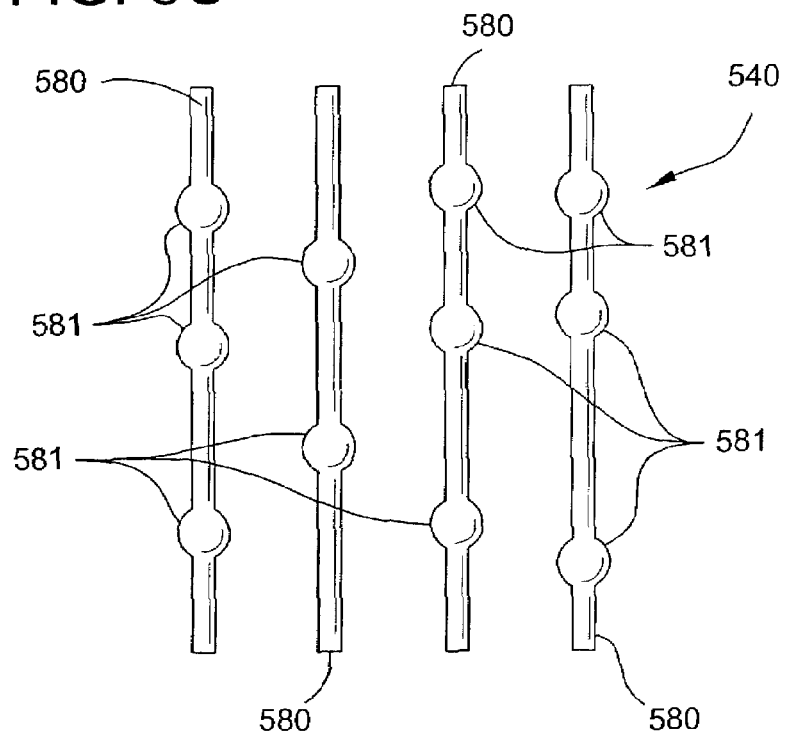
FIG. 6C is a plan view of a reinforcing member in the form of separate elongate strands having longitudinally spaced knobs thereon.

In the version shown in FIG. 6A, the strands 380 (broadly, "components" of the reinforcing member 340) each have cross pieces 381 (broadly, "projecting members") attached to the strands at locations spaced along the length of the strands. The cross pieces 381 provide additional locations for the fibers of the upper and lower regions of the absorbent core to be entangled with the reinforcing member 340 so that relative movement of the absorbent core and the strands 380 along the length of the strands is resisted. FIG. 6B shows a reinforcing member 440 in which the cross pieces 381 (of FIG. 6A) are replaced by a multiplicity of filaments 481 projecting outward from strands 480. These filaments 481 project outward from each strand 480 at locations all around the circumference of the strand. The filaments 481 would be entangled with the fibers of the upper and lower regions of the absorbent core. In a further embodiment shown in FIG. 6C, a reinforcing member 540 includes spaced apart strands 580 having bulbous portions or knobs 581 located along their length for the same purpose of resisting relative motion between the absorbent core and the strands lengthwise of the core. The strands 380, 480 and 580 themselves may be shaped and formed to further facilitate the interconnection of the strands with the fibers of the absorbent core.

Figure 6D:
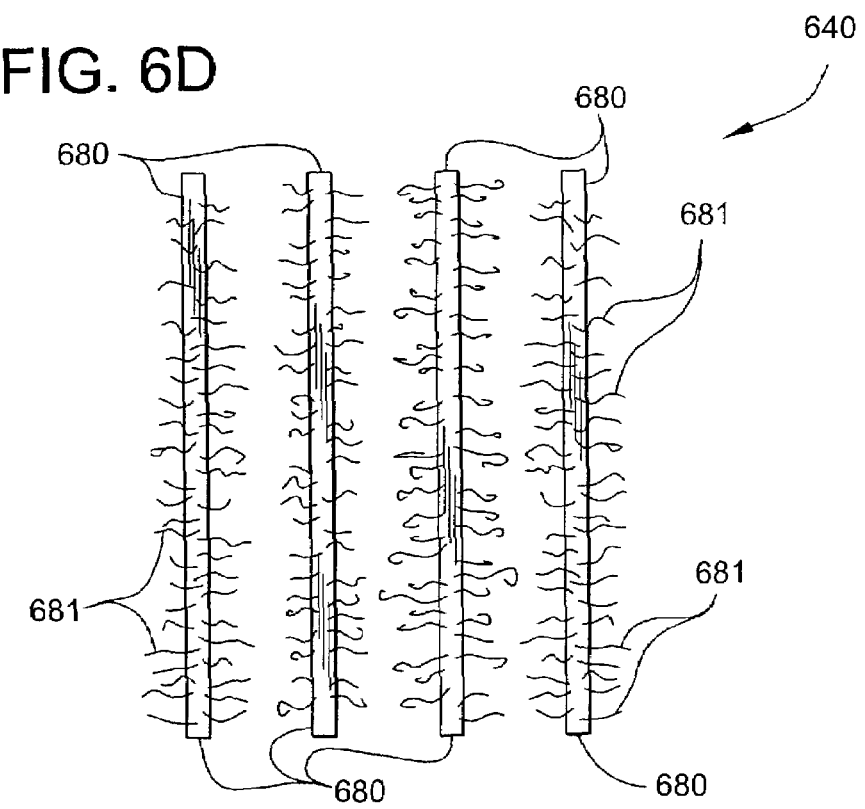
FIG. 6D is a plan view of a reinforcing member in the form of separate strips of spunbond material.

In a still further embodiment shown in FIG. 6D, a reinforcing member 640 comprises spaced apart, generally flat strips 680 of spunbond material. Each of the strips 680 has filaments 681 ("projecting members") projecting outwardly therefrom to facilitate entanglement with the fibers of the absorbent core. The filaments 681 project out not only from the peripheral edges of the strips 680, but also from the major surfaces of the strips. It is to be understood that material other than spunbond material, such as meltblown material, bonded carded web, spunlace, geometric nonwoven apertured fabrics, surge material, or even woven materials such as texturized yarn and combinations and laminations of the foregoing materials, may be used without departing from the scope of the present invention. Although the cross pieces or filaments of FIGS. 6A, 6B and 6D (381, 481, 681) are shown spaced from the adjacent strands (380, 480, 680), they may overlap adjacent strands and/or each other.

Figure 7:
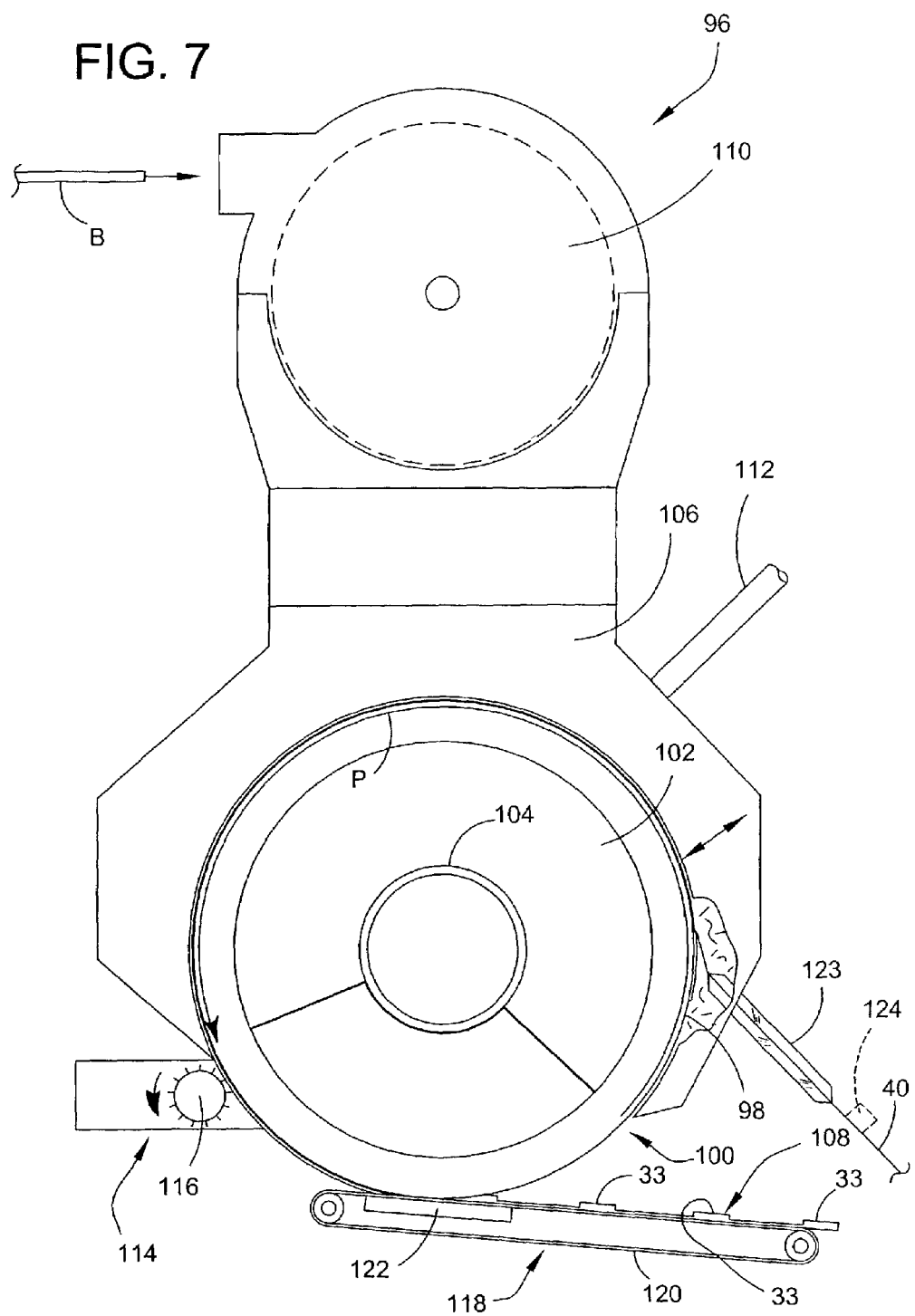
FIG. 7 is a schematic elevation of an air forming apparatus.

In one embodiment, absorbent cores having reinforcing members (340, 440, 540, 640) may be made using conventional air forming apparatus, such as the type indicated generally at 96 in FIG. 7. The apparatus 96 comprises a movable, foraminous forming surface 98 extending about the circumference of a drum (generally indicated at 100) mounted for rotation about its axis. A vacuum duct 102 located radially inward of the forming surface 98 extends over an arc of an interior diameter of the drum 100 and is arranged for drawing a vacuum under the foraminous forming surface. The vacuum duct 102 is mounted on and in fluid communication with a vacuum conduit 104 connected to a vacuum source (not shown).

The apparatus 96 further comprises a forming chamber 106 through which the forming surface 98 is movable conjointly with the drum 100 upon rotation thereof. The forming chamber 106 is configured in a conventional manner to define an interior volume to which the forming surface 98 is exposed upon movement of the forming surface through the forming chamber. More particularly, in the illustrated embodiment the forming surface 98 moves in a counter-clockwise direction along an arcuate path P within the forming chamber 106 generally from an entrance through which the forming surface enters the forming chamber substantially free of fibrous material, and an exit through which the forming surface exits the forming chamber with a web 108 of absorbent material formed thereon. Absorbent cores 33 are formed by cutting the absorbent web 108 into appropriately sized lengths.

A conventional source of fibrous material, such as a fiber supply reservoir (not shown) or a fiberizer 110 delivers a fluent fibrous material (e.g., a flow of discrete fibers) into the forming chamber 106. The fiberizer 110 shown in FIG. 7 is operatively positioned above the forming chamber 106 and can be a rotary hammer mill or a rotatable picker roll. However, it is to be understood that the fiberizer 110 may instead be located remote from the forming chamber 106 and that fluent fibrous material may be delivered to the interior of the forming chamber in other ways by other suitable devices and remain within the scope of the present invention. As an example, suitable fiberizers are available from Paper Converting Machine Company, a business having offices located in Green Bay, Wis., U.S.A.

The fibrous material may include natural fibers, synthetic fibers and combinations thereof. Examples of natural fibers include cellulosic fibers (e.g., wood pulp fibers), cotton fibers, wool fibers, silk fibers and the like, as well as combinations thereof. Synthetic fibers can include rayon fibers, polyolefin fibers, polyester fibers and the like, and combinations thereof. The fibrous material employed in the apparatus 96 of FIG. 7 is derived from a batt B of wood pulp cellulose fibers fed to the fiberizer 110 which converts the batt into discrete fibers and delivers fluidized fibrous material into the forming chamber 106.

Other fibrous or particulate material for forming the absorbent web 108 may additionally be delivered into the forming chamber 106. For example, particles or fibers of superabsorbent material may be introduced into the forming chamber 106 by employing conventional mechanisms such as pipes, channels, spreaders, nozzles and the like, as well as combinations thereof. In the illustrated embodiment, superabsorbent material is delivered into the forming chamber 106 by delivery conduit and nozzle system (which is shown schematically in FIG. 7 and indicated at 112). The fibers, particles and other desired material may be entrained in any suitable fluid medium within the forming chamber. Accordingly, any reference herein to air as being the entraining medium should be understood to be a general reference which encompasses any other operative entraining fluid.

The forming chamber 106 is supported by a suitable support frame (not shown) which may be anchored and/or joined to other suitable structural components, as necessary or desirable. The forming surface 98 is illustrated herein as being part of the forming drum 100, but it is to be understood that other techniques for providing the forming surface may also be employed without departing from the scope of the present invention. For example, the forming surface may be provided by an endless forming belt (not shown). A forming belt of this type is shown in U.S. Pat. No. 5,466,409 entitled FORMING BELT FOR THREE-DIMENSIONAL FORMING APPLICATIONS by M. Partridge et al. which issued on Nov. 14, 1995.

In operation, the vacuum source creates a vacuum in the vacuum duct 102 relative to the interior of the forming chamber 106. As the forming surface 98 enters and then moves through the forming chamber 106 along a forming path P toward the exit of the chamber, the fluidized fibrous materials and other particles within the forming chamber are operatively carried or transported by an entraining air stream and drawn inward by the vacuum toward the foraminous forming surface. Air passes inward through the forming surface 98 and is subsequently passed out of the drum 100 through the vacuum duct 102 and vacuum supply conduit 104. Fibers and other particulates are collected by the forming surface 98 as the air passes therethrough such that the collection of fibrous material forms the absorbent web 108 on the forming surface 98.

Subsequently, the forming surface 98 carrying the absorbent web 108 passes out of the forming chamber 106 through the exit to a scarfing system, generally indicated at 114 in FIG. 7, where excess thickness of the absorbent web 108 can be trimmed and removed to a predetermined extent. The scarfing system 114 includes a scarfing roll 116 for abrading excess fibrous material from the absorbent member. The removed fibers are transported away from the scarfing chamber within a suitable discharge conduit (not shown), as is well known in the art.

After the scarfing operation, the portion of the forming surface 98 on which the absorbent web 108 has been formed can be moved to a release zone of the apparatus 96 disposed exteriorly of the forming chamber 106. In the release zone, the absorbent member is drawn away from the forming surface 98 onto a conveyor, which is indicated generally at 118. The release can be assisted by the application of air pressure from the interior of the drum 100. The conveyor 118 receives the formed absorbent web 108 from the forming drum 100, and conveys the absorbent web to a collection area or to a location for further processing (not shown). Suitable conveyors can, for example, include conveyer belts, vacuum drums, transport rollers, electromagnetic suspension conveyors, fluid suspension conveyors or the like, as well as combinations thereof.

In the illustrated embodiment, the conveyor 118 includes an endless conveyor belt 120 disposed about rollers. A vacuum suction box 122 is located below the conveyor belt 120 to draw the absorbent web 108 away from the forming surface 98. The belt 120 is perforated and the vacuum box 122 defines a plenum beneath the portion of the belt in close proximity to the forming surface 98 so that the vacuum within the vacuum box acts on the absorbent web 108 on the forming surface. Removal of the absorbent web 108 from the forming surface 98 can alternatively be accomplished by the weight of the absorbent member, by centrifugal force, by mechanical ejection, by positive air pressure or by some combination thereof or by another suitable method without departing from the scope of this invention. As an example, the removed absorbent web 108 of the illustrated embodiment includes an interconnected series of absorbent cores 33, each of which has a selected surface contour that substantially matches the contours provided by the corresponding portions of the forming surface 98 upon which each individual absorbent core was formed.

The apparatus 96 and method described thus far for air forming a fibrous absorbent member is generally conventional and well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference. Other such apparatus are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, and U.S. patent application Ser. No. 09/947,128, entitled MULTI-STAGE FORMING DRUM COMMUTATOR by D. P. Murphy et al., filed Sep. 4, 2001, the entire disclosures of which are incorporated herein by reference. Examples of techniques for introducing a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference. Therefore, construction and operation of the apparatus 96 will not be further described herein except to the extent necessary to set forth the present invention.

Figure 9:
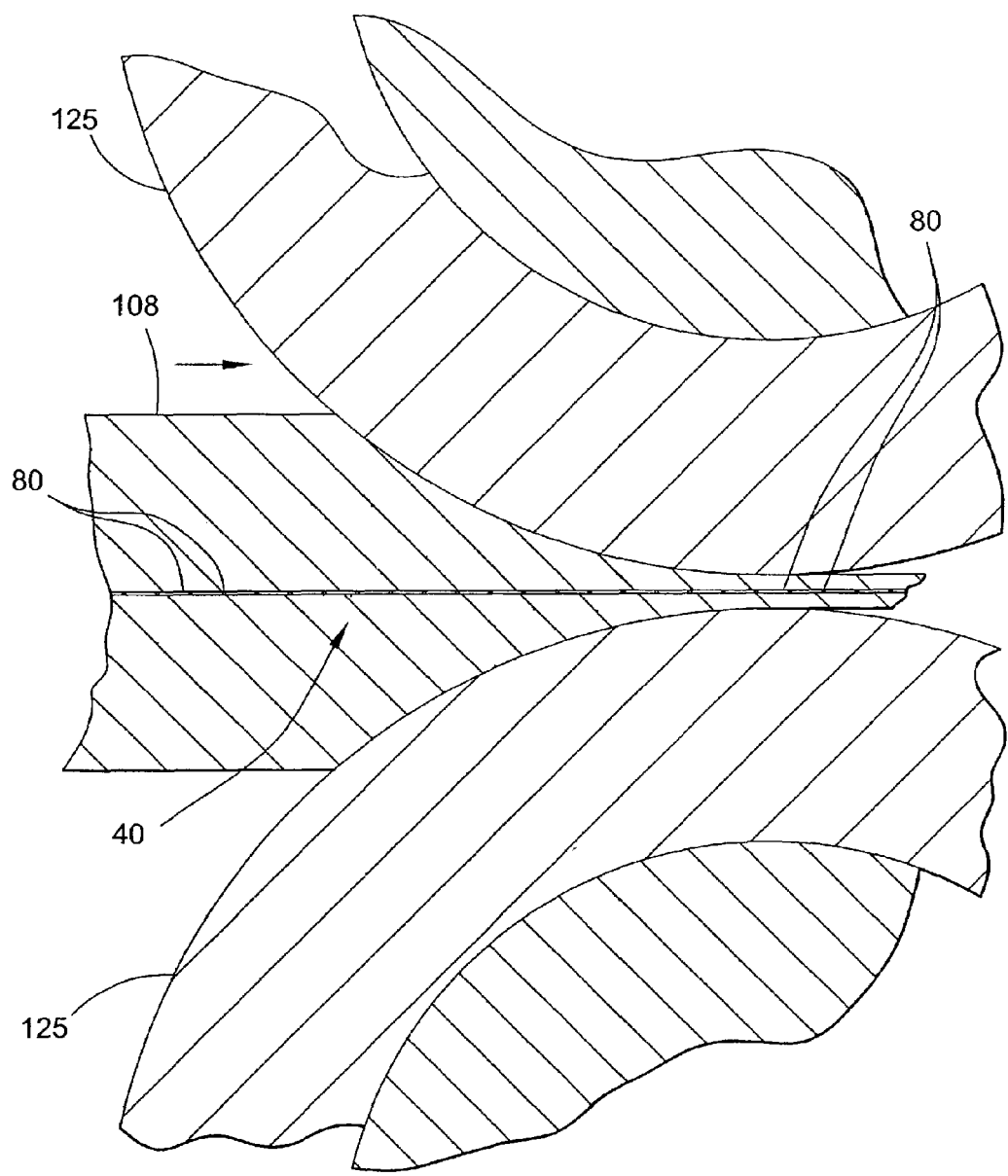
FIG. 9 is a schematic section of a web of fibrous material passing through debulking rollers.

Referring again to FIG. 7, the forming chamber 106 of the apparatus 96 further comprises a delivery tube, generally indicated at 123, through which a reinforcing member (e.g., scrim 40) is introduced into the interior of the forming chamber for incorporation into the absorbent web 108. The scrim 40 is delivered to the forming apparatus 96 in a continuous web. The scrim 40 is sufficiently porous to permit air flowing within the forming chamber 106 toward the forming surface 98 to pass therethrough. Even more desirably, the scrim is at least semi-permeable to the discrete fibers flowing within the forming chamber 106. Other fibers (92,94) become entangled with the scrim 40 by wrapping around the scrim strands 80. The force of the vacuum is believed to provide the impetus for the wrapping action of the fibers. In addition, those fibers entangled with the scrim may also become entangled with other fibers, further promoting structural unification of the fibers and scrim 40. Enhancement of the entanglement of the fibers with the web 108 is believed to be further augmented by passing the web through debulking rollers 125, as shown in FIG. 9. The debulking rollers define a nip which is considerably smaller than the thickness of the web 108 prior to entry into the nip. Thus, the web is compressed and markedly reduced in thickness by operation of the debulking rollers 125. The fibers of the web 108 undergo considerable deformation when passing through the nip of the rollers 125, especially at high speeds and significant compression. It is believed that the compaction also causes at least some additional fibers to be wrapped around the scrim strands 80, improving entanglement and hydrogen bonding of the absorbent/scrim matrix of the web 108. Moreover, fibers that are already somewhat wrapped around the strands 80 can be further secured to the strands and to the resulting stabilized matrix. In one embodiment, the absorbent core 33 has a density in the range of 0.06 to 0.5 g/cc. It is believed the scrim 40 would have particular advantage in cores having densities in excess of about 0.2 g/cc, which are typically more susceptible to cracking.

To form an absorbent core having a reinforcing member comprising distinct strands 380 of FIG. 6A the web of scrim 40 is fed through a cutter 124 (illustrated in phantom in FIG. 7) just before entering the forming chamber 106. As illustrated, the cutter 124 is positioned immediately upstream from the delivery tube 123. The cutter 124 cuts the unitary scrim web lengthwise into individual strands 380. It is also possible to feed a continuous web of spunbond material to the cutter 124, which would cut the material into the strips 680 (FIG. 6D). It is also envisioned that the strands 480 and 580 (FIGS. 6B and 6C) could be initially unitary and then cut apart upon entry into the forming chamber 106. By keeping the scrim 40 (or other reinforcing member) in a unified web until just before entry into the forming chamber 106, the reinforcing member (340,440,540,640) is much easier to handle. Cutting a unitary, two dimensional web into separate strands helps to keep the reinforcing member embedded in an absorbent core from becoming entangled with the scarfing roll 114 of an absorbent core forming apparatus (e.g., as shown in FIG. 7). This is because some or all of the CD strands which are more likely to be entangled or otherwise caught on the scarfing roll, are cut away.

To improve the containment of the high-absorbency material, absorbent structure 32 can include an overwrap, such as a wrap sheet 74, which is placed immediately adjacent and around the absorbent core 33 and may be bonded to the absorbent core and to the various other components of the diaper (FIG. 2). The wrap sheet 74 is preferably a layer of absorbent material which covers the major bodyside and outerside surfaces of the absorbent core 33, and preferably encloses substantially all of the peripheral edges of the absorbent core to form a substantially complete envelope thereabout. Alternatively, the wrap sheet 74 can provide an absorbent wrapping which covers the major bodyside and outerside surfaces of the absorbent core 33, and encloses substantially only the lateral side edges of the absorbent core. Accordingly, both the linear and the inwardly curved portions of the lateral side edges of the wrap sheet 74 can be closed about the absorbent core. In such an arrangement, however, the end edges of the wrap sheet 74 may not be completely closed around the end edges of the absorbent core 33 at the waistband regions of the article.

For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the absorbent core 33. Such a configuration of the wrap sheet can, for example, facilitate the formation of a substantially complete sealing and closure around the peripheral edges of the absorbent core 33. In the back waistband portion of the illustrated diaper 10, the absorbent wrap 74 may also be configured to extend an increased distance away from the periphery of the absorbent core 33 to add opacity and strength to the back side-sections of the diaper 10. In the illustrated embodiment, the bodyside and outerside layers of the absorbent wrap 74 can extend at least about ½ inch beyond the peripheral edges of the absorbent structure to provide an outwardly protruding, flange-type bonding area over which the periphery of the bodyside portion of the absorbent wrap may be completely or partially connected to the periphery of the outerside portion of the absorbent wrap.

The bodyside and outerside layers of the wrap sheet 74 may be composed of substantially the same material, or may be composed of different materials. For example, the outerside layer of the wrap sheet 74 may be composed of a relatively lower basis weight material having a relatively high porosity, such as a wet strength cellulosic tissue composed of softwood pulp. The bodyside layer of the wrap sheet 74 may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

In desired arrangements, a spacer layer 76 may be interposed between the absorbent structure 32 and the backsheet layer 30 to provide desired benefits (FIG. 2). Where the backsheet layer 30 is vapor permeable, for example, the spacer layer 76 can operatively locate and separate the backsheet layer 30 away from the absorbent structure 32 by a discrete distance. The resultant spacing distance can help to reduce a damp or cool feeling that may arise when the absorbent becomes wetted.

In the various attachments and securements employed in the construction of the article of the invention, it should be readily apparent that any conventional attachment or securement technique may be employed. Such techniques may, for example, include adhesive bonds, cohesive bonds, thermal bonds, sonic bonds, pins, staples, rivets, stitches or the like, as well as combinations thereof.

The following examples are representative, and are presented to provide a more detailed understanding of the invention. The examples are not intended to limit the scope of the invention.

Tests were performed to establish the improvement of reinforced absorbent cores of the present invention over traditional, non-reinforced absorbent cores. Absorbent cores having reinforcing members in the form of scrim were incorporated into diapers otherwise of the same construction as diapers sold under the trademark HUGGIES® ULTRATRIM® by Kimberly Clark Corporation of Neenah, Wis. These diapers were tested along with conventional HUGGIES® ULTRATRIM® or HUGGIES® SUPREME® diapers in several confidential studies.

EXAMPLE 1

Absorbent articles in the form of diapers were constructed with a reinforced absorbent core as summarized in Table 1. Other than the reinforced absorbent core, the diapers had substantially the same construction as a STEP 4 HUGGIES® ULTRATRIM® diaper available from Kimberly Clark Corporation. The absorbent core of all of the diapers was contoured in two dimensions, but of substantially uniform thickness (i.e., a flat pad).

TABLE 1

| Absorbent core; "Pad" (fibrous matrix, 33) | Superabsorbent particles in a fibrous matrix of wood pulp fluff. Shaped pad with a substantially uniform basis weight of about 750 gsm, target density of about 0.22 g/cc. Pad length of about 378 mm and narrowest width in crotch of about 3 inches (76 mm) |
|---|---|
| Weight of wood pulp fluff | 13 grams; fluff basis weight is approximately uniform across pad |
| Wood pulp fluff material | CR 1654; available from US Alliance, Coosa Pines, Alabama, |
| Weight of superabsorbent material | 12 grams |
| Superabsorbent material | FAVOR SXM 9543; available from Stockhausen, Inc.; Greensboro, North Carolina, U.S.A. |
| Scrim Material | RO3230 Polypropylene Scrim material available from Conwed Plastics, a business having offices in Minneapolis, Minnesota; Mesh Size = 9 × 8 mm; Tensile Strength 69N/10 cm MD; 49N/10 cm CD; basis weight = 4.64 gsm; width of 52 mm |

"gsm" = gram per square meter
"CD" = lateral, cross-direction (26)
"MD" = longitudinal, machine-direction (24)

These diapers were tested along with STEP 4 HUGGIES® ULTRATRIM® diapers of the same configuration but without the scrim material in a confidential study involving 56 children. The participants were given both kinds of diapers identified only by code letter, and with no indication whether the diaper absorbent core was reinforced or unreinforced. Ten diapers of each type (reinforced and unreinforced) were provided and were used in succession in normal use over a period of five days and then the participants were surveyed. For respondents with a preference for one of the two diaper types, the scrim containing diaper was preferred 3:1. The top two reasons for preferring the diaper having the reinforced absorbent core of the present invention were related to absorbent core integrity.

EXAMPLE 2

Absorbent articles were made in the form of test diapers having the construction of a STEP 3 HUGGIES® ULTRATRIM® diapers. The Step 3 diapers have a "zoned" absorbent core, meaning different regions of the core have different basis weights. A higher basis weight region of the absorbent core is provided by an increased thickness of the core in that region. The absorbent core of the test diapers was formed with reinforcing scrim according to the present invention. Material parts of the diaper construction are summarized in the following Table 2.

TABLE 2

| | |
|---|---|
| Absorbent core; "Pad" (fibrous matrix, 33) | Superabsorbent particles in a fibrous matrix of wood pulp fluff. Shaped pad with a zoned, higher basis weight in the crotch region of the diaper. Higher basis weight (900 gsm) region to lower basis weight (425 gsm), target density of about 0.22 g/cc. Pad length of about 363 mm and narrowest width in crotch of about 89 mm |
| Weight of wood pulp fluff | 13.9 grams; |
| Wood pulp fluff material | CR 1654 available from US Alliance, Coosa Pines, Alabama, |
| Weight of superabsorbent material | 10.7 grams |
| Superabsorbent material | FAVOR SXM 9543; available from Stockhausen, Inc.; Greensboro, North Carolina |
| Scrim Material (40) | RO3230 Polypropylene Scrim material available from Conwed Plastics, a business having offices in Minneapolis, Minnesota; Mesh Size = 9 × 8 mm; Tensile Strength = 69N/10 cm, MD; 49N/10 cm CD; basis weight = 4.64 gsm; width of 52 mm |

The test diapers were tested along with standard STEP 3 HUGGIES® ULTRATRIM® diapers of the same configuration but without the reinforcing scrim material in a blind study involving 24 children. Both the test diaper and the standard diaper included at least 18 diapers for evaluation. Each of the children was given at random either a test diaper or a standard diaper to wear overnight. If urine or BM leakage occurred, the diaper was removed and replaced with a standard diaper. The test diaper was still returned to the test site, but not evaluated. If no BM or urine leakage occurred, the children returned to the test site the next morning and the diaper was removed. The child's skin was inspected for gel (i.e., the superabsorbent) from the diaper. The diaper was evaluated for absorbent core integrity, and photographed on a light box. Diaper fluid loading was also measured. A dry test diaper was put on the child who was allowed to move about in a play environment for about 90 minutes. The play environment is selected to expose the diaper and the absorbent core therein to increased forces tending to tear apart the absorbent core. The diaper was removed, evaluated and photographed in the same way as the diaper used for overnight. The same procedure was followed on another night and subsequent day using diapers having an absorbent core of the present invention. The results of the evaluations and measurements for this test are given in the following Table 3.

TABLE 3

| | Average Fluid Absorbed | Average Gel on Skin Rating | Average Pad Integrity Rating |
|---|---|---|---|
| Daytime Diapers | | | |
| Code R (control) | 47.69 | 1.00 | 3.11 |
| Code S (scrim) | 43.49 | 0.28 | 1.76 |
| Overnight Diapers | | | |
| Code R (control) | 202.53 | 2.63 | 2.34 |
| Code S (scrim) | 167.2 | 1.65 | 1.68 |

The ratings for gel on skin were judged by inspectors on a scale from 0 to 5. A rating of 0 means that there is no gel on the skin and a rating of 5 means that there was a lot of gel on the skin. The absorbent core integrity rating was given by inspectors from a scale of 1 to 5. The guidelines for integrity ratings are as follows:
 1=good integrity and intact
 2=bunching and clumping, but not split
 3=core split at front or back, one split only
 4=core split at both front and back, two splits
 5=totally disintegrated The reference to "front" and "back" refers to the front and back (or top and bottom) major surfaces of the absorbent core.

As may be seen by reference to Table 3, the scrim reinforced absorbent core significantly outperformed the conventional, unreinforced diaper absorbent core. The rating for gel on skin and core integrity for the diaper constructed according to the present invention were markedly superior to the conventional, unreinforced diaper.

EXAMPLE 3

Another test compared scrim reinforced diapers to conventional, unreinforced diapers using substantially the same protocol as described in Example 2. However, it is noted that the test subjects had a greater level of activity during "play", thus subjecting the absorbent cores to greater forces detrimental to their integrity. At least 20 of each of the scrim reinforced and conventional diapers were evaluated. The unreinforced or control diaper was a STEP 4 HUGGIES SUPREME® diaper available from Kimberly Clark Corporation. The STEP 4 diaper has an extensible backsheet layer. The test diapers had the same construction as the control diaper except for the provision of the scrim in the absorbent core. The following Table 4 gives the general properties of the diapers.

TABLE 4

| | |
|---|---|
| Absorbent core; "Pad" (fibrous matrix, 33) | Superabsorbent particles in a fibrous matrix of wood pulp fluff. Shaped pad with a zoned, higher basis weight in the crotch region of the diaper. Higher basis weight (1250 gsm) region to lower basis weight (550 gsm), Pad narrowest width in crotch of about 89 mm |
| Weight of wood pulp fluff | 17.3 grams; |
| Wood pulp fluff material | CR 1654 available from US Alliance, Coosa Pines, Alabama, |
| Weight of superabsorbent material | 13.3 grams |
| Superabsorbent material | FAVOR SXM 9543; available from Stockhausen, Inc.; Greensboro, North Carolina |
| Scrim Material (40) | RO3230 Polypropylene Scrim material available from Conwed Plastics of Minneapolis, Minnesota; Mesh Size = 9 × 8 mm; Tensile Strength = 69N/10 cm MD; 49N/10 cm CD; basis weight = 4.64 gsm; width of 52 mm |

To establish the crack or integrity rating for each used diaper, the diaper was removed from the child and manually stretched out on top of a light box. The diapers were then assessed for cracking on the scale of 0-3 as follows:
 0=no cracks
 1=slight crack
 2=moderate cracking (one large crack or several small cracks)
 3=severe cracking (major separation or very large number of small cracks)

Reference is made to FIGS. 10A-10D, showing different diapers stretched over a light box. The darker region on the left side of the figures is a higher basis weight ("zoned") area of the absorbent core. Each of the illustrated diapers were assessed a different rating. Cracking is observed as a lighter area relative to the immediately surrounding area.

Figure 10A:
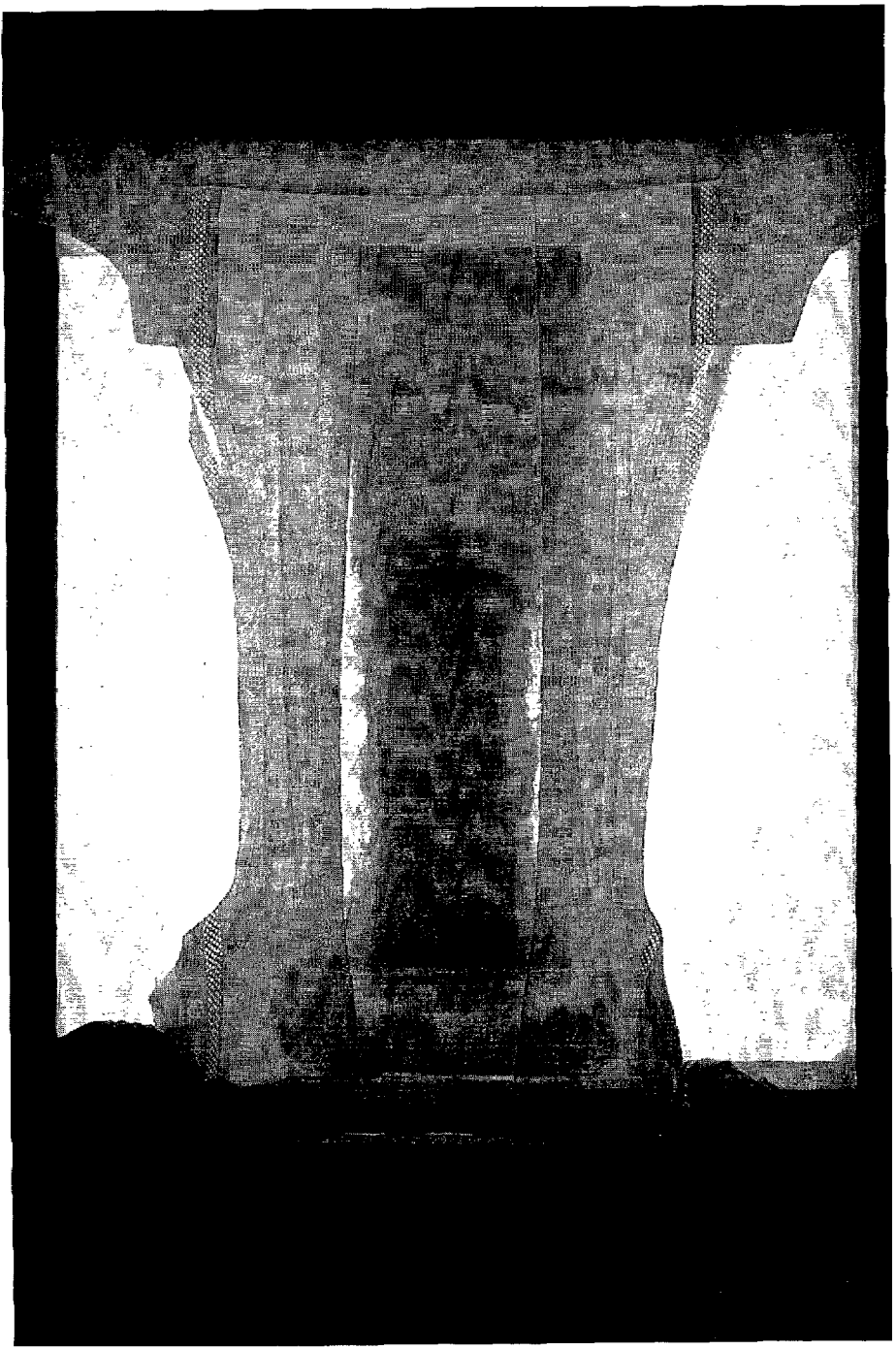
FIGS. 10A-10D are photographs of diapers disposed on a light box for evaluation of absorbent cores of the diapers.
Figure 10B:
Figure 10C:
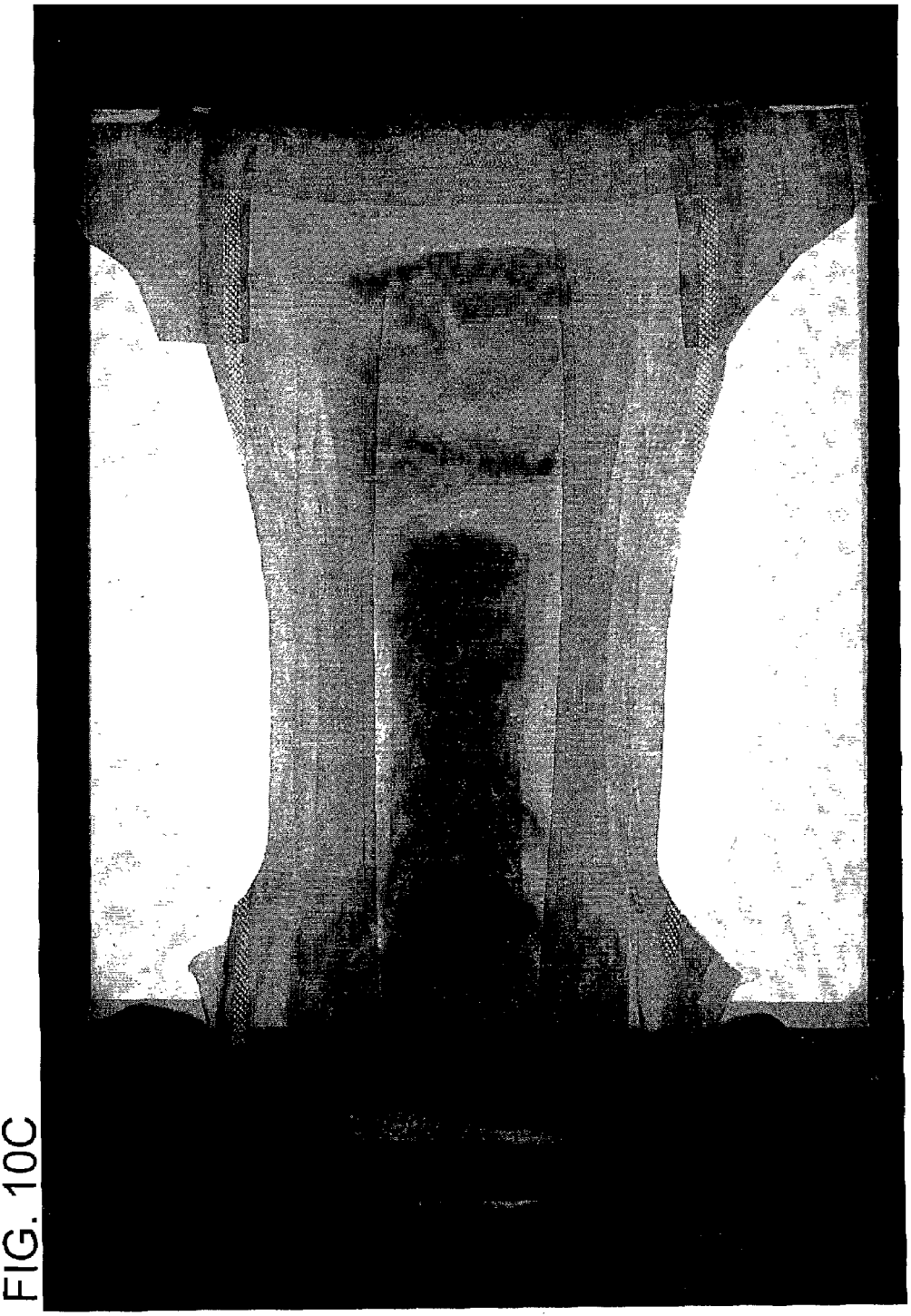
Figure 10D:
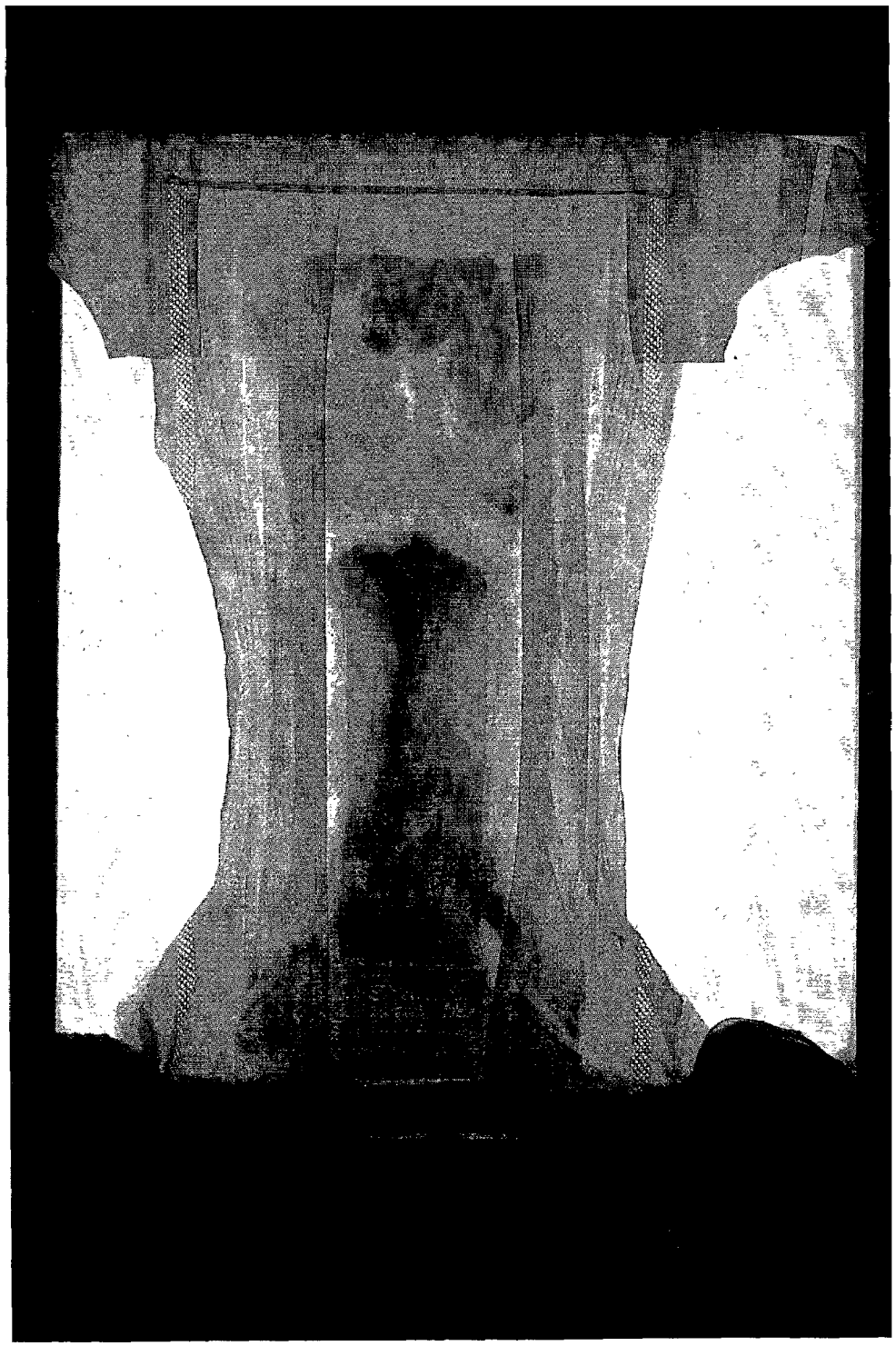

Referring to FIG. 10A, a scrim reinforced diaper is shown. This diaper was given a rating of 0. No cracks are observed in this diaper. The diaper shown in FIG. 10B was given a rating of 1, having a slight crack seen in the lower basis weight area generally along the central longitudinal axis of the diaper. The diapers of FIGS. 10B-10D are all not reinforced with scrim or any other reinforcing material (i.e., having the form of conventional diapers). The diaper in FIG. 10C was given a rating of 2, having one clearly observable large crack and several small cracks. The large crack extends transversely of the absorbent core, generally at the intersection of the lower and higher basis weight areas, which is known to be a prime location for cracking. Several other small cracks can be seen in the lighter basis weight area. FIG. 10D shows a diaper having a rating of 3. The diaper has a major separation of two portions of the absorbent core, at a location generally at the intersection of the lower and higher basis weight areas. A substantial number of additional, smaller cracks may also be observed in the lower basis weight region. It is to be understood that the foregoing examples are representative of diapers corresponding to particular ratings. The exact appearance of the diapers given a particular rating varied from those shown in the figures.

The rating for the diapers is given in Table 5.

TABLE 5

| Code Description | Average Maximum Pad Integrity Rating | |
|---|---|---|
| | Day-Play time | Night |
| C: control | 1.9 | 1.2 |
| S: scrim | 1.0 | 0.6 |

Photographs of each diaper were taken for a quantitative integrity value based on gray scale analysis. These results agreed with the visually assessed crack ratings given in Table 5.

EXAMPLE 4

Another test compared not only scrim reinforced diapers to conventional, unreinforced diapers, but also diapers having scrim of different sizes and configurations. The configurations of the diapers tested are given in the following Table 6.

TABLE 6

| | SCRIM SIZE | | | SCRIM WIDTH | |
|---|---|---|---|---|---|
| | Small | Medium | Large | 52 mm | 26 mm |
| L | | X | | | X |
| K | | X | | X | |
| T | X | | | X | |
| M | | | X | X | |
| U | | | | | |

As shown in Table 6, the various diapers were given letter codes, most of which are readily apparent in their meaning from the table. Diaper U is a conventional STEP 4 HUGGIES® ULTRATRIM® diaper available from Kimberly Clark Corporation of Neenah, Wis. The absorbent core of this diaper is not reinforced with scrim. The narrowest part of the crotch width of the absorbent in a STEP 4 HUGGIES® ULTRATRIM® diaper is about 94 mm. The absorbent core is zoned with a higher basis weight region in the crotch region of the diaper of about 1300 gsm and a lower basis weight region of about 390 gsm. The scrim reinforced diapers (L, K, T, M) had essentially the same construction as the STEP 4 HUGGIES® ULTRATRIM® except for the provision of the scrim.

All of the scrim used was made of polypropylene and purchased from Conwed Plastics of Minneapolis, Minn. Properties of the small, medium and large scrim specified in Table 6 are given in the following Table 7

TABLE 7

| | Small R06277 | Medium R03230 | Large R04035 |
|---|---|---|---|
| Mesh Size (MD × CD) (mm × mm) | 4 × 4 | 9 × 8 | 36 × 19 |
| Basis Weight (gsm) | 7.09 | 4.64 | 7.1 |
| MD Tensile Strength (N/10 cm) | 75 | 69 | 104 |
| CD tensile strength (N/10 cm) | 73 | 49 | 65 |
| Minimum Strand Diameter (microns) | 124 | 181 | 304 |
| Weighted Average Diameter (microns) | 234 | 286 | 531 |
| Percent Open Area | 90 | 92 | 96 |

The mesh size is the spacing (in both the machine-direction 24 and the cross-direction 26) between strands in millimeters. The tensile strengths are given per 10 cm, because the tested samples were 10 cm in width. The minimum strand diameters for each type of scrim material were determined using an Axioplan 2 Imaging microscope, having a Epiplan NeoFluar 1.25× objective, and a 10.5 mm×8.3 mm field of view. The microscope is available from Carl Zeiss MicroImaging, Inc. having an office in Thornwood, N.Y. All images were autoscaled, delineated, cleaned (scrap and fill), and thresholded to prepare images for analysis. Locations on the imaged strands to take diametrical measurements were defined visually by the technician, selecting the apparently thinnest extent of each strand. The manually defined line scans were then segmented and measured automatically.

The percent open area of the scrim is a ratio of the open area of the scrim over the total area occupied by the scrim. The measurements were made using a Zeiss KS400 Image Analysis System, available from Carl Zeiss MicroImaging, Inc. having an office in Thornwood, N.Y. Images were captured using an Axiocam CCD camera (1300×1030 pixels), 8 bit grayscale, available from Carl Zeiss MicroImaging, Inc., employing a 50 mm Nikon lens (Nikon Corporation of Japan), set to f/2.8 and employing a variable neutral density filter. The scrim was illuminated for measurement by a transmitted fluorescent light box having a sample stage located about 25 cm above the light box. The location of the camera lens was about 26 cm above the stage and the field of view was 44 mm×35 mm.

The open area of each opening in the scrim was segmented automatically by the analysis system. To find the total area (open area plus the area of the strands), the strand image was skeletonized, inverted and segmented, essentially to eliminate the strand from the image except for its centerline. A method for determining total area was developed for this particular situation where there are relatively few openings per image, all of substantially the same size. Conventionally, the total open area is equated to the total open area of the frame of the image. However in this case, a cell was defined which includes the open area of a single scrim opening (82), as well as a fraction of the strands surrounding the open area. The fraction for the strands on the top, bottom and sides of the opening was about 50%, because about one half of the area of each of these strands is associated with two scrim openings. At the corners, the fraction was 25%, because each corner is associated with four openings. The open area fraction is then the individual open areas divided by the corresponding cell area. The open area fractions were calculated to 95% confidence intervals. In one embodiment, the percent open area of the scrim is at least about 75%, more preferably at least about 90% and still more preferably at least about 92%.

The weighted average diameter measurements were made from the same images used for the open area fraction. The weighted average diameter includes junctions of strands and so is not equivalent to the diameter of individual strands. The morphology of the scrim, for many reasons including necking of the strands, is complex. Therefore a weighted average diameter was calculated. The area of the feature observed was divided by one half of the perimeter of the feature (which for thin strands is approximately the length). The result is a weighted average diameter of the strands which takes into account the thicker junctions where two strands intersect.

The diapers were subjected to the same testing protocol as in Example 2, again by 24 subjects. At least 17 diapers were evaluated for each code. The results are shown in the following Table 8.

TABLE 8

| | Average Fluid Absorbed (grams) | Average Cracking Rating | Average Bunching & Clumping Rating |
|---|---|---|---|
| Daytime Diapers | | | |
| Code U | 56.34 | 1.58 | 2.37 |
| Code T | 68.34 | 0.71 | 1.65 |
| Code M | 56.81 | 0.82 | 1.68 |
| Code L | 31.00 | 0.74 | 1.84 |
| Code K | 49.11 | 0.43 | 1.71 |
| Overnight Diapers | | | |
| Code U | 125.70 | 0.57 | 1.95 |
| Code T | 120.69 | 0.29 | 1.35 |
| Code M | 146.35 | 0.45 | 1.60 |
| Code L | 153.93 | 0.48 | 1.48 |
| Code K | 152.20 | 0.22 | 1.17 |

Instead of a single rating, absorbent core integrity was broken down into a rating for cracking and a rating for bunching and clumping. The rating was determined by an evaluator using the following guideline ratings for cracking (same as in example 3):

0=no cracks
1=slight crack
2=moderate cracking (one large crack or several small cracks)
3=severe cracking (major separation or very large number of small cracks)

The rating for bunching and clumping was assigned using the following guidelines:

0=no bunching or clumping
1=slight bunching or clumping
2=moderate bunching and clumping
3=severe bunching and clumping Four categories of ratings were made for evaluation, by breaking down the cracking and the bunching and clumping ratings into "daytime" and "overnight" categories. As expected, the scrim diapers having a scrim reinforced absorbent core outperformed the conventional, unreinforced diaper. Both the small and medium scrim outperformed the larger scrim. The wider scrim at 52 mm performed better than the scrim having a width of 26 mm. More strands in the CD direction provide more strands for fiber entanglement with and around the scrim. The medium sized scrim at 52 mm performed better than all other codes in 3 of the 4 categories.

As stated previously herein, entanglement of fibers used to form the absorbent core with strands of the scrim connects the scrim and fibers together in a robust fibrous web 108 (from which the absorbent cores 33 are formed). Entanglement is believed to occur at the time the scrim reinforced fibrous web is formed in the air forming apparatus 96 (FIG. 7). It is believed that some of the fibers moving past the scrim 40 toward the forming surface of the drum 100 are captured by one or more strands 80 of the scrim. More particularly, the fibers (92,94) wrap around the strand 80, thereby connecting themselves to the scrim 40. It is also believed that other fibers become connected by entanglement, not with the strand 80, but with another fiber (92 or 94) already entangled on the strand.

Figure 8A:
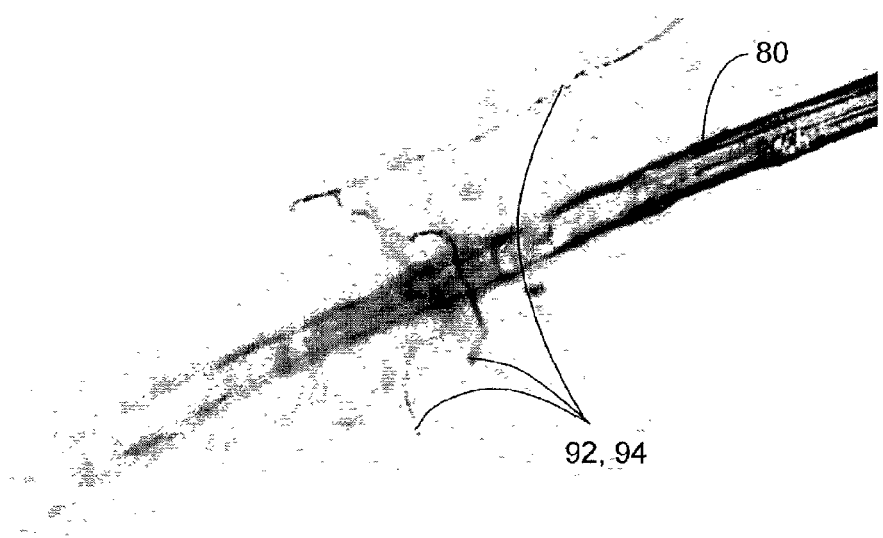
FIGS. 8A-8C are photographs of a strand of scrim having fibers entangled thereon.
Figure 8B:
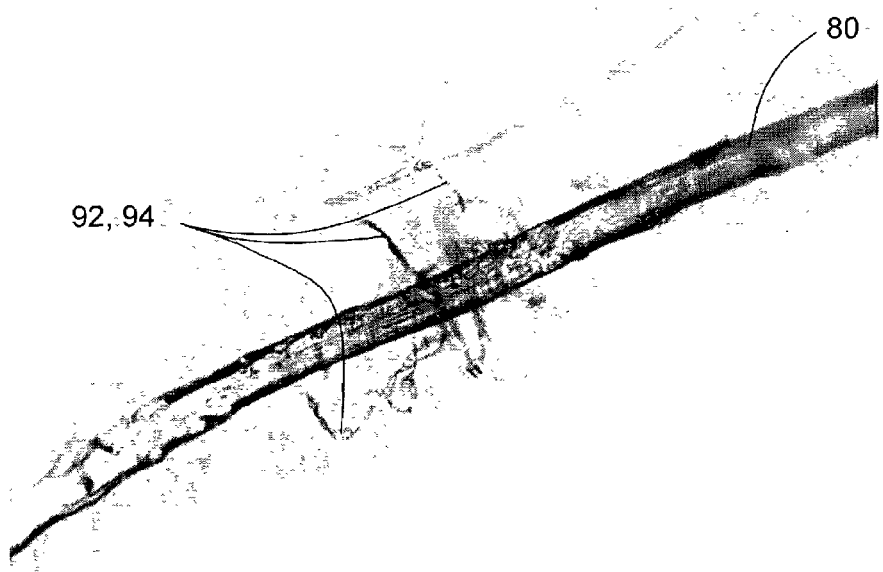
Figure 8C:
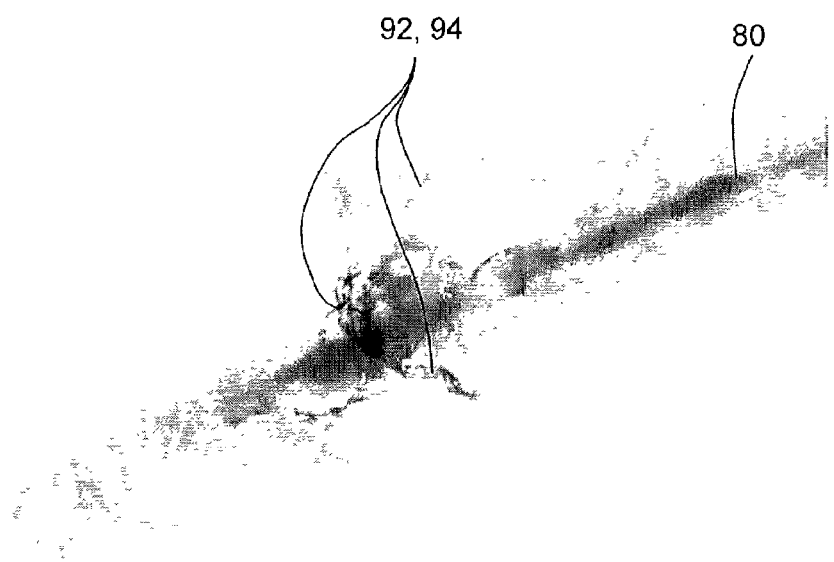

FIGS. 8A-8C are highly magnified photographs of a strand 80 of scrim 40 removed from a fibrous web air formed generally as described hereinafter. The fibers 92,94 shown on the strand 80 remain attached after the majority of the fibers were forcibly removed from the scrim. These fibers show themselves to be wrapped around the strand 80 and with each other. FIG. 8A is a digital photograph with the focal plane being above the strand 80 (thus, fibers above the strand are more clearly focused). The focus of the photograph of FIG. 8B is in the plane of the strand 80, so that fibers (or portions thereof) more nearly in that plane are more sharply focused. Finally, the photograph of FIG. 8C is focused below the plane of the strand so that fibers below the plane of the strand are more clearly focused. All of the photographs were taken at a magnification of about 60×. Thus, it will be understood that there are portions of fibers all around the strand, illustrating the wrapping effect.

Tests were conducted to evaluate the amount of entanglement as a function of the size of the openings in the scrim being used. It is believed that there is an optimum mesh size and/or scrim fiber size for given processing conditions and material properties of the scrim and absorbent materials. It was noticed that the smallest mesh size (Code T) in Example 3 was embedding itself more to the screen side, causing the scrim to lie very close to the surface of the pad. It is believed that the fibers did not pass as easily through the smaller mesh screen, with most of the fibers forming on top of the screen.

In a controlled experiment, a small handsheet former was used to deposit fibers on a band of scrim. The handsheet former is disclosed in co-assigned U.S. patent application Ser. No. 09/814,402 entitled HIGH SUPERABSORBENT CONTENT WEBS AND A METHOD FOR MAKING THEM by Singh et al., filed Mar. 22, 2001. A corresponding PCT application was published Oct. 3, 2002 as publication number WO02076520. The disclosure of both applications is incorporated herein by reference. It is noted that the handsheet forming employs a vacuum to draw fluidized fibers down onto a forming surface, analogous to the forming chamber described in FIG. 7. In this case, the scrim itself constitutes the forming surface. A pressure of about 138 kilopascals (20 psi) was applied to jets of air in an agitation chamber. A vacuum of 0.25 kilopascals (1 inch of water) was drawn from the bottom of the forming chamber and maintained a negative pressure in both the agitation chamber and the forming chamber. A 52 mm wide piece of each scrim size was placed across a 74 mm diameter forming chamber. The scrim was cut to maximize the number of strands in the cross-direction 26. About one gram of fiberized pulp or one gram of a combination of pulp and SAM was directed at the scrim. The amount of fiber (or fiber and SAM) that was entangled with, protruding through (entangled with scrim or other fibers) and laying on top of the scrim was measured. Table 9 below catalogs the percentage amount of scrim which was retained on the scrim of each size.

TABLE 9

|  | Small RO6277 | Medium RO3230 | Large RO4035 |
|---|---|---|---|
| % Retained CR1654 | 52.6 | 26.4 | 1.6 |
| % Retained CR1654/SAM (60/40) | 44.4 | 13.2 | 0.6 |
| % Retained Sulfatate-HJ | 6.4 | 4.8 | 0.4 |
| % Retained Caressa 1300 | 28.4 | 15.2 | 0.8 |

The three different scrim materials employed are identified in the columns and the properties of these are given above in Table 5. In one instance 100% CR1654 fibers were used having a length weighted average fiber length of about 2 mm. A mixture of CR1654 fibers and superabsorbent material (SAM) in proportion 60% to 40% was used in another test for all three scrim materials. In another set of tests, Sulfatate-HJ fibers were used. Sulfatate-HJ is a hardwood fiber having a length weighted average fiber length of about 0.9 mm, and is available in the United States from Rayonier Inc. of Jessup, Ga. Caressa 1300 is a chemically treated softwood pulp available from Buckeye Technologies, Inc. a company having offices in Memphis, Tenn., USA. The length weighted average fiber length of the Caressa 1300 fiber is about 2.9 mm. However, the Caressa 1300 fiber is much stiffer than the CR1654 fiber.

It will be readily apparent from the table that the CR1654 fiber achieved the most retention on the scrim for all scrim material sizes. It is acknowledged, that when a combination of CR1654 fiber and SAM was deposited on the scrim, significantly less fiber was entangled on the scrim. It is believed that the high retention of CR1654 on the scrim was because of entanglement of the CR1654 fibers with the strands of the scrim. The significant level of entanglement is believed to be the result of two factors. One is the length of the CR1654 fiber and the second is its flexibility. The ratio of pulp fiber length to cell wall thickness (i.e., thickness of the fiber wall) is sometimes used as an index of relative fiber flexibility. However, a more satisfactory indication of fiber flexibility is provided by fiber coarseness. Coarseness values reflect the weight of the fiber wall material per unit fiber length, calculated in milligrams per 100 meters (see, Smook, G. A. *Handbook for Pulp & Paper Technologists*, Joint Textbook Committee of the Paper Industry, 1988.). It is noted that one way to establish coarseness of fibers is by TAPPI test T-234. The combination of fiber length of the CR 1654 and greater flexibility (lower coarseness) relative to the Caressa 1300, promotes the wrapping of the fiber around at least one of the strands 80 of the scrim 40. Fibers which were shorter (Sulfatate HJ) and less flexible (Caressa 1300) did not demonstrate as much retention on the scrim in the test. Process conditions such as vacuum pressure may also affect the amount of entanglement and/or placement of the scrim web in the z-directional thickness of the absorbent structure.

Preferably, fibers used in making the absorbent core of the present invention have a length in the range of 0.4 to 5 mm, and coarseness in the range of about 5 to 28 mg/100m. However, it is to be understood that fibers having lengths and coarsenesses (stiffnesses) outside the aforementioned ranges may be used without departing from the scope of the present invention.

Not surprisingly, the scrim having the largest mesh (RO4035) retained the least fiber, and the smallest mesh scrim (RO6277) retained the most. However, retention of fiber is not the only criteria in selecting a fiber to be used. The smaller mesh scrim is difficult to precisely and repeatedly place in a thickness direction of an air formed fibrous web. In one embodiment, the scrim has minimum mesh size (measured along a strand 80 between adjacent junctions in either the machine direction 26) of 0.5 mm and a maximum mesh size in the cross-direction 26 equal to the narrowest width of the absorbent core 33. Preferably, the reinforcing member would have two or more strands extending in the machine-direction 24. The aspect ratio of the mesh size (the ratio of mesh size in the machine-direction 24 over the mesh size in the cross-direction 26) could be in the range of between 0.01 and 100 and more preferably between about 0.5 and 1.2. In another embodiment, the strands 80 have a minimum diameter (or about two times a minimum spacing between adjacent openings 282 shown in FIG. 5B) which is less than the length weighted average length of the fibers (including the length weighted average length of both absorbent and/or any non-absorbent fibers in the core 33) to facilitate entanglement of the fibers with the scrim 40. Thus, the strands 80 must be small enough and/or the fibers long enough to permit them to wrap completely around the strand. However, it is to be understood that scrim having mesh sizes outside the aforementioned range could be used without departing from the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent structure for absorbing liquid comprising an absorbent member including an upper region and a lower region, the upper and lower regions each being at least partially made of fibers, and a reinforcing member located between the upper region and the lower region for maintaining the structural integrity of the absorbent member, the reinforcing member being permeated by fibers from the upper region to the lower region and from the lower region to the upper region, at least some of the permeating fibers from each of the upper and lower regions being entangled with fibers in the other of the upper and lower regions to facilitate interconnection of the upper and lower regions and the reinforcing member wherein the absorbent member has at least two zones of different basis weights.

2. An absorbent article as set forth in claim 1 wherein the reinforcing scrim is liquid permeable.

3. An absorbent article as set forth in claim 2 wherein the reinforcing scrim has preformed openings therein receiving the fibers through the reinforcing scrim.

4. An absorbent article as set forth in claim 3 wherein the openings are generally rectangular in shape.

5. An absorbent article as set forth in claim 3 wherein the reinforcing scrim comprises strands arranged in a pattern in which at least some of the strands intersect one another.

6. An absorbent article as set forth in claim 5 wherein at least some of the strands are secured together where they intersect each other.

7. An absorbent article as set forth in claim 5 further comprising a coating of superabsorbent material on at least some of the strands.

8. An absorbent article as set forth in claim 5 wherein at least some of the strands are formed from a superabsorbent material.

9. An absorbent article as set forth in claim 3 wherein the ratio of open area of the reinforcing scrim to a total area of the reinforcing scrim is greater than or equal to about 75%.

10. An absorbent article as set forth in claim 9 wherein the ratio of open area of the reinforcing scrim to the total area of the reinforcing scrim is greater than or equal to about 90%.

11. An absorbent article as set forth in claim 10 wherein the ratio of open area of the reinforcing scrim to the total area of the reinforcing scrim is greater than or equal to about 92%.

12. An absorbent article as set forth in claim 1 wherein the reinforcing scrim comprises strands having a minimum diameter which is less than a length weighted average length of the fibers.

13. An absorbent article as set forth in claim 1 wherein the reinforcing scrim comprises sheet material.

14. An absorbent article as set forth in claim 1 wherein the reinforcing scrim comprises spaced apart components unconnected to each other except through connection with an upper region of the absorbent core and a lower region of the absorbent core.

15. An absorbent article as set forth in claim 14 wherein each component has projecting elements extending outwardly from the component.

16. An absorbent article as set forth in claim 15 wherein the components comprise thin, flat strips of material.

17. An absorbent article as set forth in claim 16 wherein the strips of material are nonwoven spunbond material.

18. An absorbent article as set forth in claim 16 wherein each of the projecting elements comprises a multiplicity of filaments.

19. An absorbent article as set forth in claim 15 wherein the components comprise at least two strands extending generally lengthwise of the absorbent structure.

20. An absorbent article as set forth in claim 19 wherein each projecting element comprises a crosspiece arranged generally perpendicularly to the strand.

21. An absorbent article as set forth in claim 19 wherein each of the projecting elements comprises a multiplicity of filaments.

22. An absorbent article as set forth in claim 15 wherein each projecting element comprises a knob.

23. An absorbent article as set forth in claim 1 wherein the reinforcing scrim has longitudinal edge margins covered by the fibers of the absorbent core.

24. An absorbent article as set forth in claim 1 wherein the fibers comprise absorbent fibers.

25. An absorbent article as set forth in claim 24 wherein the absorbent fibers comprise cellulosic fibers.

26. An absorbent article as set forth in claim 25 wherein the absorbent fibers have a length weighted average length in the range of about 0.5 mm to 5 mm.

27. An absorbent article as set forth in claim 23 wherein the fibers further comprise nonabsorbent fibers.

28. An absorbent article as set forth in claim 1 wherein the fibers comprise nonabsorbent fibers.

29. An absorbent article as set forth in claim 1 wherein the absorbent core has a minimum width and wherein the reinforcing scrim has a width which is 25% to 100% of said minimum width of the absorbent core.

30. An absorbent article as set forth in claim 29 wherein the width of the reinforcing scrim is 50% to 100% of said minimum width of the absorbent core.

31. An absorbent article as set forth in claim 1 wherein the absorbent structure has a density in the range of about 0.06 g/cc to about 0.5 g/cc.

32. An absorbent article as set forth in claim 31 wherein the absorbent structure has a density greater than about 0.2 g/cc.

* * * * *

UNITED STATES PATENT AND TRADEMARK OFFICE
CERTIFICATE OF CORRECTION

PATENT NO. : 7,745,687 B2
APPLICATION NO. : 10/306086
DATED : June 29, 2010
INVENTOR(S) : David W. Heyn et al.

Page 1 of 1

It is certified that error appears in the above-identified patent and that said Letters Patent is hereby corrected as shown below:

In the Claims, Claim 1, column 28, lines 51-65, delete

"An absorbent structure for absorbing liquid comprising an absorbent member including an upper region and a lower region, the upper and lower regions each being at least partially made of fibers, and a reinforcing member located between the upper region and the lower region for maintaining the structural integrity of the absorbent member, the reinforcing member being permeated by fibers from the upper region to the lower region and from the lower region to the upper region, at least some of the permeating fibers from each of the upper and lower regions being entangled with fibers in the other of the upper and lower regions to facilitate interconnection of the upper and lower regions and the reinforcing member wherein the absorbent member has at least two zones of different basis weights."

and insert therefore

-- An absorbent article adapted to be worn generally at the lower torso to capture body exudates, the absorbent article comprising a liquid permeable liner, a backsheet layer and an absorbent structure disposed between the liner and the backsheet layer, the absorbent structure comprising an absorbent core including fibers and reinforcing scrim, the scrim being connected to the fibers by entanglement of the fibers with the scrim, entanglement of fibers with other fibers entangled with the scrim and entanglement of fibers with each other where at least one of the entangled fibers passes through the scrim. --

Signed and Sealed this
Twenty-sixth Day of November, 2013

Margaret A. Focarino
*Commissioner for Patents of the United States Patent and Trademark Office*